(12) United States Patent
Hilbi

(10) Patent No.: US 7,629,130 B2
(45) Date of Patent: Dec. 8, 2009

(54) BACTERIAL PROTEIN PHOSPHOINOSITIDE PROBES AND EFFECTORS

(75) Inventor: Hubert Hilbi, Zurich (CH)

(73) Assignee: Eidgenossisch Technische Hochschule Zurich Eth, Zurich (CH)

( * ) Notice: Subject to any disclaimer, the term of this patent is extended or adjusted under 35 U.S.C. 154(b) by 271 days.

(21) Appl. No.: 11/525,334

(22) Filed: Sep. 23, 2006

(65) Prior Publication Data

US 2008/0227697 A1 Sep. 18, 2008

Related U.S. Application Data

(60) Provisional application No. 60/719,934, filed on Sep. 23, 2005.

(51) Int. Cl.
| | |
|---|---|
| C12Q 1/00 | (2006.01) |
| G01N 33/53 | (2006.01) |
| G01N 33/563 | (2006.01) |
| G01N 33/543 | (2006.01) |
| G01N 33/531 | (2006.01) |
| G01N 33/533 | (2006.01) |

(52) U.S. Cl. .............................. 435/7.1; 435/4; 435/7.7; 436/513; 436/518; 436/543; 436/546

(58) Field of Classification Search ........................ None
See application file for complete search history.

(56) References Cited

OTHER PUBLICATIONS

Bowie et al. Science vol. 247, No. 4948, p. 1306-1310,1990.*
Lazar et al. Molecular and Cellular Biology, Mar. 1988, p. 1247-1252.*
Burgess et al. The Journal of Cell Biology, vol. 111, Nov. 1990 2129-2138.*
Bork (Genome Research, 2000,10:398-400).*
Weber, Stefan S. et al., "*Legionella pneumophila* Exploits (PI(4)P to Anchor Secreted Effector Proteins to the Replicative Vacuole," PLoS Pathogens, www.plospathogens.org., vol. 2, Issue 5, pp. 0001 to 0013 (May 2006).

* cited by examiner

*Primary Examiner*—David J Blanchard
*Assistant Examiner*—Oluwatosin Ogunbiyi
(74) *Attorney, Agent, or Firm*—Janet Sleath; Speckman Law Group PLLC

(57) ABSTRACT

Methods for detecting and quantifying phosphoinositide lipids in a sample are provided, together with novel SidC- and SdcA-derived polypeptide fragments, or fusion proteins comprising such fragments that may be effectively employed as PI(4)P probes in biochemical and cell biological assays. Applications of the disclosed probes include: (i) detection and quantification of PI(4)P in vitro; and (ii) staining of intracellular compartments in live or fixed eukaryotic cells.

8 Claims, 18 Drawing Sheets

Figure 1:
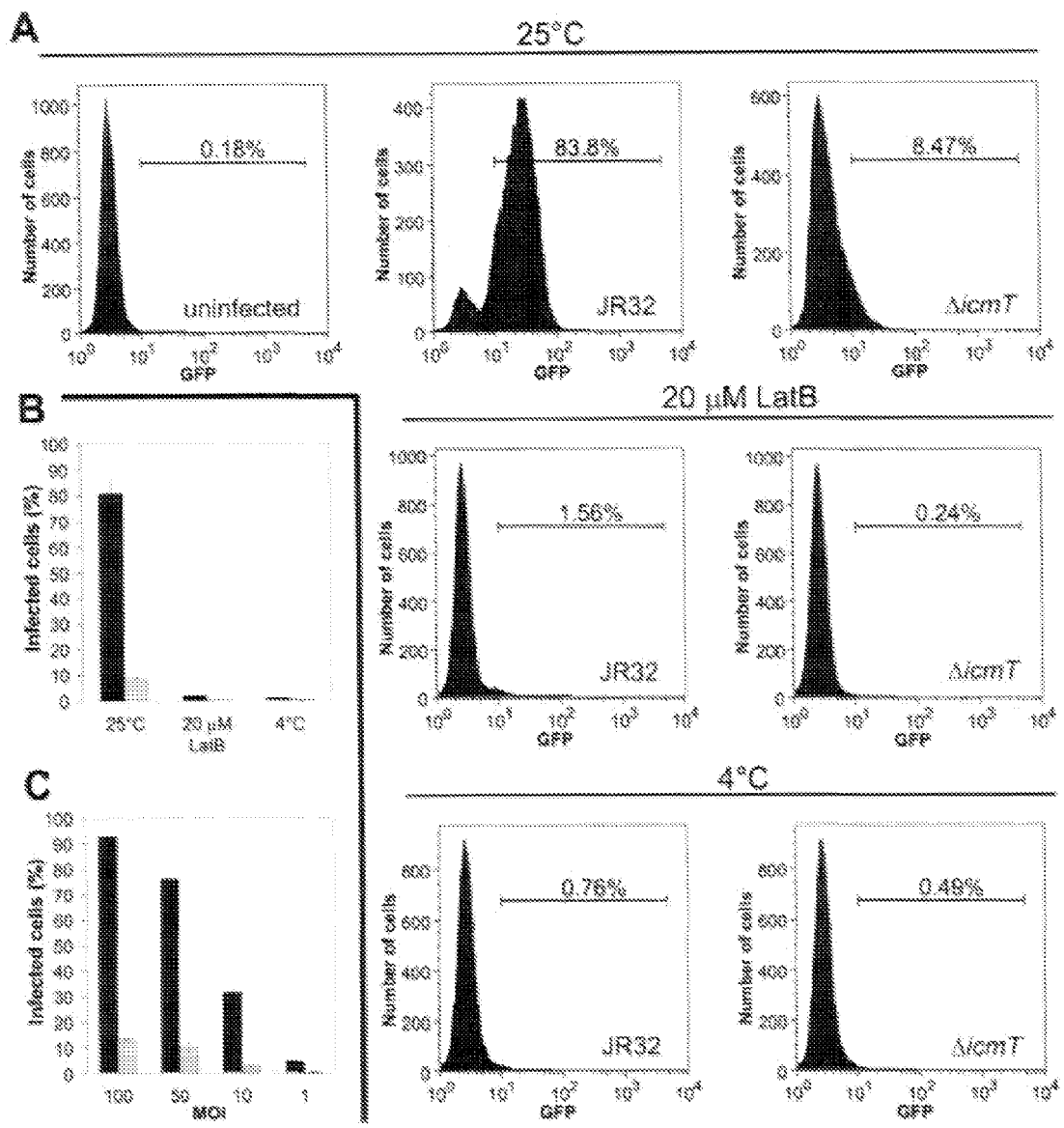

```
   1 atggtgataa acatggttga cgtaatcaaa ttcaaagagc cggaacgttg tgattatcta
  61 tatgttgatg aaaacaacaa agttcatatc cttttaccga ttgtaggagg agatgaaata
 121 ggcctggata atacctgtca aacagcagtt gagttgatca cattttctg tggtagtgcc
 181 cacagtggtg tgactaaata ttctgctgaa caccaactca gtgaatacaa aaggcaattg
 241 gaagaagaca tcaaagccat caatagtcaa aagaaaattt cacctcatgc ttatgacgat
 301 ttattaaaag agaaaataga acgcttacag caaattgaaa aatacattga attaattcaa
 361 gtactaaaaa aacaatatga tgaacaaaat gatatcaggc aacttcgtac tggagggatt
 421 ccgcaattac cctctgggt aaaggaaatc attaaatcct ctgaaaatgc tttcgctgtg
 481 agactttctc catatgacaa cgataaattc actcgctttg atgacccttt attcaatgtc
 541 aaaagaaaca tctcaaaata tgacacgccc tcaagacaag ctcctattcc aatatacgag
 601 ggattaggtt atcgcctgcg ttcaacactg ttcccggaag ataaaacacc aactccaatt
 661 aataaaaaat cacttaggca taagttaaa agcactgttc ttagtcatta taaagatgaa
 721 gatagaattg atggagaaaa aaaagatgaa aaattaaacg aactaattac taatcttcaa
 781 aacgaacttg taaaagagtt agtaaaaagt gatcctcaat attcgaaact atctttatct
 841 aaagatccaa gaggaaaaga aataaattac gattatttag taaatagttt gatgcttgta
 901 gataacgact ctgaaattgg tgattggatt gatactattc tcgacgctac agtagattcc
 961 actgtctggg tagctcaggc atccagccct ttctatgatg gtgctaaaga aatatcatca
1021 gaccgcgatg cggacaagat atccatcaga gttcagtacc tgttggccga agccaatatt
1081 tactgtaaaa caaacaaatt atcggatgct aactttggag aattttcga caaagagcct
1141 catgctactg aaattgcgaa aagagtaaag gaaggattta cgcaaggtgc agatatagaa
1201 ccaattatat acgactatat taacagcaac catgccgagc tgggattaaa atctccgtta
1261 accggcaaac aacaacaaga aatcactgat aaatttacaa acattataa tacgattaaa
1321 gaatctccac attttgatga gttttttgtc gctgatccgg ataaaaaagg caatatcttt
1381 tctcatcaag gcagaatcag ttgtcatttt ctggattcct ttactcgaca aaccaaaggc
1441 aaacatcctc ttggtgatct tgcaagtcat caggaagctc tccaggaagg aacctccaat
1501 cgcttacatc acaagaatga ggtagtagcc caggggtacg aaaaactgga tcaattcaag
1561 aaagaggttg tcaaactgct ggctgagaat aaaccaaaag aattattgga ttatttggtt
1621 gctacctcac ctacaggtgt tccaaattac tccatgcttt cgaaggaaac tcaaaattac
1681 attgcttata atcgtaactg gccagccatt caaaaagagc tggaaaaggc taccagcatc
1741 ccggagagtc aaaaacaaga tctttcaaga ttgctttctc gtgataattt acaacacgat
1801 aatctaagcg caattacctg gtcaaaatat tcctccaagc cattattgga tgtggaatta
1861 aataaaatcg ctgaaggatt agaactcact gcaaaaattt acaatgaaaa gagaggacgc
1921 gaatcgtggt taaaggttc aagaaatgaa gctcgtaaga cccatgtga agaattgcaa
1981 agagtatcca aagaaatcaa tactcttctg caaagtgaat ctttaacgaa aagccaggta
2041 cttgaaaagg ttttaaattc tatagaaaca ttagataaaa ttgacagaga catttctgcc
2101 gaatccaatt ggtttcaaag tactctgcaa aaggaagtca ggttatttcg agatcaattg
2161 aaagatattt gccaattgga caagtatgcc tttaaatcaa caaaacttga tgaaatcatc
2221 tctctggaaa tggaagaaca atttcaaaag atacaagatc ctgctgttca acaaattgtc
2281 agggacttgc cttctcattg ccacaatgat gaagcaattg aatttcttaa gacattgaac
2341 cctgaagagg cagcaaaagt agctagctat ttaagcctgg aatacaggga aattaataaa
2401 tcaaccgata agaaaactct cctagaacaa gatattccca cactgtttaa agaagtcaat
2461 acgcagttac tctccaaact caagaagaa aaagctattg atgagcaagt tcatgaaaaa
2521 ctcagtcaac tggctgacaa aattgcccct gagcatttta caagaaataa cattataaaa
2581 tggtctacca accctgaaaa gcttgaggaa tcaaatctta atgagccaat caaatcagtc
2641 caaagcccta ctactaaaca aacatcaaaa caattcaggg aagcgatggg tgaaatcact
2701 ggaagaaatg agcctcctac agacactttg tacacgggaa ttataaagaa atag
```

FIGURE 9

```
   1 gtgatgaaca tggttgacaa aataaaattc aaagagccgg agcgatgcga atatttacat
  61 atcgctaagg ataataaagt ccatattctt ttaccuattg taggtgggga tgaaatagga
 121 ctggataata cctgtgaaac aacaggtgag ttattaacct ttttctatgg aaaaacgcat
 181 ggtgggacaa agtattctgc tgaacatcac ctaaatgaat ataaaaagaa tctggaagat
 241 gatataaagg caatcgtgt tcaagaaaaa atttcaccaa atgcctatga agatctatta
 301 aaagagaaaa aagagcgcct ggaacaaatc gaaaaatata ttgatttaat caaagtactc
 361 aaagagaaat ttgatgagca aagagaaata gacaaactac gcacagaagg aatcccgcaa
 421 ttaccttctg gagtaaagga agtcattaaa tcttctgaaa atgcctttgc tttaaggctt
 481 tccccgcata gaccagactc atttacccgc tttgatgatc ctctgtttag tctcaaaaga
 541 aacagatctc aatatgaagc tgggggatac caacgggcaa ctgatggatt agggctcgt
 601 ttgcgttctg agcttctacc accagataaa gacactccta ttgttttaa taaaaaatca
 661 ctgaaggaca aaatcgtaga ttctgtttta gtgcaacttg acaaagattt taatacaaaa
 721 gatggcgatc gtggtcaaaa atttgaggat ataaaaaaac tcgttctaga agagtacaag
 781 aaaattgatt ccgaacttca agtggatgag gatacctatc accaaccact taacttggat
 841 tatttggaaa acatagcatg tacgttagat gacaactcca ccgcgaaaga ttgggtttat
 901 ggaattattg gtgctacaac agaagctgat tattggccaa aaaaggaaag tgaaagtggt
 961 actgaaaaag ttagtgtatt ctatgagaag caaaaggaaa taaaatttga atctgataca
1021 aatacaatgt caattaaagt ccaatatcta ttagctgaga ttaattttta tgtaaaacc
1081 aacaagttat cagatgctaa cttcggtgaa tttttgata aagagcccca tgctactgaa
1141 gttgctaaaa gagtgaaaga aggacttgtt caaggagcag agattgagcc tattatttac
1201 aattacatta acagccacca tgccgaactg ggattaacat ctgagttaag cagcaagcaa
1261 caagaggaaa ttactgaaaa atttactcaa cgttatcaca ttattgagaa ctctcctcac
1321 tttgatgaat tttttgtcgc tgatcctgat aaaaaggga atatattctc ccatcaaggc
1381 agaatgagtt gccatttcct ggatttcttc gctcgacaaa ccaaaggcaa atatcccctt
1441 ggtgatcttg caggtcatca agaagcactc caggcaggaa cttccaatcg gttacatcac
1501 aagaatgagg tagtcgctca aggatatgaa aaatttgatc aattcaagaa agaagtcgtc
1561 aaactgctgg cagagagtaa accaaaagaa ttattggatt atttggttgc tacctccccc
1621 acaggtgttc ctaattattc catgctctca aaggaaactc aaaattatat tgcttacaac
1681 cgtaactggc cagccattca aaaagagctc gaaaaaacta ctgacatacc agagaaccaa
1741 aaacaagatc ttttaagatt gcttctcgt aataatctgc aacacgagaa cctcagtgca
1801 attacctggt caaaatactc ttccaagcca ttattggatg tggagttaaa taaaatcgcc
1861 gaaggtttag atctaactgc taaaatttac aatgaaaaaa gaaaaagtga atggtttaaa
1921 ggttcaagaa atgaggctcg taagacccaa tgtgaagaat tgcaaagagt atcccaagaa
1981 atcaatgctc ttctgcaaag tgaatcttta acaaaaagcc aagttcttga aaaagtttta
2041 aactccatag aagcattgga taaattgat agagacattt ctgctgaata taatttattt
2101 aagagtactc tgcaaaaaga agtacaatca tttcgagatc aattgaagga tatctgtcaa
2161 ttagataact atgcctttaa atcaacaaaa cttgatgaaa ttatctctct ggaaatggaa
2221 gaacaattic aaatgattaa agatcctgct gtcaacaaaa ttgtccgaga ctgccttct
2281 cattgtcata ataatgaagt gattgaattc tttatgacat taaatcctga agaagcagct
2341 aaagtagcta gctatttaag cctcgagtac cggaactca ataaatcaac agataagaaa
2401 actctccttg aacaagatat tcctaaatta tttaagaag tgaatatgga actattatcc
2461 caattaaaac aagatagtgc agttaaggaa gacgtctatg aaaaattctg tcaattagct
2521 gataaaattc ctcctgagca ttttacaagg aataatatca ggaaatggtc tgccaatcct
2581 gaaaaacttg aggagtccaa tctcggtgaa ttactaaaat cctctgaagg ctcaattact
2641 gaaatggcaa gaaaatacag agaaaccata aatgaaatga caggaagaaa tgagtcactc
2701 agagaaactg ttaggaatac aatatag
```

FIGURE 10

```
   1 mneiilhlmn eistltppin plnlkqifss tllpegkapv evesqlnlll likkyvdeys
  61 slaeeqeeyk rkkhkldevm kkgeelqrki sdlakkieha knelnplyke iepkanevls
 121 kqnplappyk fpeygevqks ivvghysylf ktskeiettr akiklvllkn kwnalmadls
 181 qfgiqppvee davdslqkfi aaveleikkl tracekwdel qkrfakqlsa tdinkkesel
 241 ekqielllkd vgrietvvtn hslapdlkae ltrkfqesed tqgliqeyqn qidgllsnfn
 301 psswlswysd snysdnqqkl knsvsflqll aqqkelkikh helvkqqeil ikaipetpsn
 361 eedisiykkl vpdaidline ipiesipnfv lpsglsydss padfylvlli lmpkvsekke
 421 qfsqaleklq empalgkqiq qlrsgydlpi tmdvqlpslq eaeeskdsln eedplkeelk
 481 sqiklcqsyl etakqidllm kdhgqttnea kalieqlrli snqplknedi nsikedlstl
 541 anqiqslvse lnqiplpnls gekidpplek qeiavdktip ltvelmhpaq viqigndspi
 601 ekqqldneee tpvvleslrp rpvihkeses itqklqvdng qempvvldst ctpqaihkel
 661 estteklqvd ngheipvvle strspqiiht esesvgkkqh veveqeipvt lelirpssmv
 721 ekdsvatvek qqvterqetp ivlestrlsp mvqkdtglsg ekqhkeieqe isvvteltph
 781 tqvvrqgses sleqqvpngq etlavvkssp seplrpstpe vpaisrkpng lslfnghdel
 841 sednilaffd eagnqisiss eedsetftvd rgkvissgid kafkekpvst gheldklsnp
 901 qhqesapsis plppssillk qkldsfhvqn meyikqhsee iqlwykglyd aaqsscvnea
 961 lglkalhllk dilfelknqn dlsvllaykr mcpnplqdiq nilrlkpalp ivdesideeq
1021 qlknwpeelq kfhqqyvkik kehpleaelf iqaihslisi khlmelpdak tsnreampii
1081 tqdpryeplk rhrgfirawe yiedffrmli gkltgqdeye yskrpcffkt rshrlleevd
1141 tilhsmapts s
```

FIGURE 11

```
   1 mliyqgkeiv rfkektggkn ksdvdgfykd ndggkffikk pgdprelfte lfaglllkef
  61 mkrglidesy fpslicadvi qfedksygli cplvsfdelh kvigtssgdg kdrntlketl
 121 fgpgyyagit kqnkyfglsm almfslllga hsvhsgnivv lngeekeksk qfgridwgda
 181 fryfahprnn dnllyayenr gwfnyksltk dyflnykkin glfpamaeka rqlqsklnpe
 241 llvkivtsal knipadlide ktkiqlaaym cmdsfkeatf gtegnckdfa iamatllenr
 301 lgkiavlkdm splsnpeely qsilelkplt llmtsstsfs etinqwadil kttdmekfsf
 361 dsnpinllel vkqfnlyvde laitceannv wakeridstp nlfalydnsg geaihghafv
 421 pyykesivlr riftvdpntf nlsrfaafeg pcqlyckehk dsawvkiqtl ltlgngiint
 481 lkiikqaqaf gideavtenl kalkeqfiaf qlaeadikes lkapsfaepl pnkeseffyp
 541 idekalakmn gyqlaticle elnspkpspl ierilsnkkf wkrinsafes gvfkgrtddp
 601 agkiakirew hqllqisgkk tagqidelqk ivislqskik rqtiefeele atliqikeky
 661 qllekmaeqs ehekssaqsi irslnlelsq iklqlqeqek lqfqlkelke kiheqttlsk
 721 rlgeelqtgk ktnthqeeti qritkeksla dssleslrke lhelakkers lhktleekql
 781 qvqqleeqla ekekenlalk kadkqsqhek sldksaiesl tselnqlkle lqkqetlqlq
 841 lkslrkqiqe qtlvveglke elqkqkksnt hqeetierit keksladsal eslrkemyel
 901 trkneenqlk ltkqvhslse qleekqlqir efekqlqeke krveqsekgk asakrtvasl
 961 reqvsnlklq lqqlgeviqe kekgsslisq qskqiialqe iiedqkrqle elkikiqelv
1021 sanqelqkqn qslskenlhn kntvedlkkk lnelnvqleq lhqssnekeq tirklreeli
1081 kkdsslkqne emqlaqkhlq eeidrlqkei kqqqlntnql esilaqskea ekryqqalqq
1141 kkgiyfarme rvspiylqiq qieqkakele erreteasta aktlatklrl eiknyldnne
1201 sdeksalnsf kinakrhien sketlnqhre ewkyllanvt lgvfllqigy laailinkat
1261 tgnytffsqt nsgkkldale kaissthset lvyg
```

FIGURE 12

```
  1 aqmalqrnin lqnqqdrmeh elfkrrlmaa lflwylskks haaekvkeii reynekaikn
 61 aekaskpsqq stsstsqadk eiqkmldeye qaikraqeni kkgeelekkl dkl
```

FIGURE 13

```
   1 mileeyirma knkeffdale eiaesaknde tlrnelakvl ddilktdpsd peafrkivae
  61 hqefwdehdp slmefnegrf fgksrkqylk sddflnstdp tynfqklhqf aaeqrvklgl
 121 eksdtdtlva ilknnpeecr ayieskkpgl gnfsegnvhg wlkeeytpti ppkainkstg
 181 vlsdeaikri keqardllll klinssgntq llkdlrdams kpeaeraana lgfpteqnqv
 241 lflsrevvda leervekleq eaakrgfdsy vqsishnall akknqlestt aagfknslde
 301 pyktylpese weraqgvlga rylqavlssg tqnlkdalna kdanalitel kkpallgphd
 361 yidkavteen lgslkknmmk sfinnikdet nlkaldalka ldgaknldkf kevlgklgit
 421 padwvkdtdl kdmkqwarar qfeleinrvs slgsgahskl mstltklpve kqreilakpq
 481 qlrhlmnaye shvaehylgk nasgiaellt enkrlegfra ihnaevarvl anfkpeitln
 541 dkqvaainqa lttansnpnt ytqatdykil idaiktqsgs vnqkdfynaf nlnddgraft
 601 sstprkdems kqqqhnqhiy aeynstsnsg nkkllavlls iekpvtfskd ivnrflrplk
 661 dsetpqdyad tlfgenptnp ankkfkddll reltptvfne ikndlrkqel ldtnpahvmt
 721 aikalstele sikgitgpir tnacklkfin didpvhlynp tfqgtarska aqmkeryegl
 781 srdcglvvdq lrrqvvaleg hlkslpkege fkaagltleq kaeikklrtd leaelsavre
 841 dldfykkiqg kletivkevd vaakgkmhyy ynsegikrhp pvsrdqippl pnvpnpslrs
 901 sttattgsng riqeflvgek ipeqqivvvd vshktapksg apvetigryt qdnnvpdqvt
 961 skkgeiskvp gskfeilqfp tqvpppnpps gdplveakvn fsmamaadil asldspptkd
1021 kpirlrgsnp eeleylytal vilgeknpkf kfnrdaievn savfhpdnvk grlwgfssns
1081 lysqvftntg ltetqniiqs kikhmqqmtd ekfspqkere kvdskvqeit dkqskmkkel
1141 npvhkttert ieqegpapes pstgmrk
```

FIGURE 14

SEQUENCE LISTING

<160> NUMBER OF SEQ ID NOS: 18

<210> SEQ ID NO 1
<211> LENGTH: 169
<212> TYPE: PRT
<213> ORGANISM: L. pneumophila

<400> SEQUENCE: 1

Ser Lys Tyr Ser Ser Lys Pro Leu Leu Asp Val Glu Leu Asn Lys Ile
1               5                   10                  15

Ala Glu Gly Leu Glu Leu Thr Ala Lys Ile Tyr Asn Glu Lys Arg Gly
            20                  25                  30

Arg Glu Trp Trp Phe Lys Gly Ser Arg Asn Glu Ala Arg Lys Thr Gln
        35                  40                  45

Cys Glu Glu Leu Gln Arg Val Ser Lys Glu Ile Asn Thr Leu Leu Gln
50                  55                  60

Ser Glu Ser Leu Thr Lys Ser Gln Val Leu Glu Lys Val Leu Asn Ser
65                  70                  75                  80

Ile Glu Thr Leu Asp Lys Ile Asp Arg Asp Ile Ser Ala Glu Ser Asn
                85                  90                  95

Trp Phe Gln Ser Thr Leu Gln Lys Glu Val Arg Leu Phe Arg Asp Gln
            100                 105                 110

Leu Lys Asp Ile Cys Gln Leu Asp Lys Tyr Ala Phe Lys Ser Thr Lys
        115                 120                 125

Leu Asp Glu Ile Ile Ser Leu Glu Met Glu Glu Gln Phe Gln Lys Ile
    130                 135                 140

Gln Asp Pro Ala Val Gln Gln Ile Val Arg Asp Leu Pro Ser His Cys
145                 150                 155                 160

His Asn Asp Glu Ala Ile Glu Phe Phe
                165

<210> SEQ ID NO 2
<211> LENGTH: 168

```
<212> TYPE: PRT
<213> ORGANISM: L. pneumophila

<400> SEQUENCE: 2

Ser Lys Tyr Ser

-continued

```
gaccgcgatg cggacaagat atccatcaga gttcagtacc tgttggccga agccaatatt   1080
tactgtaaaa caaacaaatt atcggatgct aactttggag aatttttcga caaagagcct   1140
catgctactg aaattgcgaa aagagtaaag gaaggattta cgcaaggtgc agatatagaa   1200
ccaattatat acgactatat taacagcaac catgccgagc tgggattaaa atctccgtta   1260
accggcaaac aacaacaaga aatcactgat aaatttacaa aacattataa tacgattaaa   1320
gaatctccac attttgatga gttttttgtc gctgatccgg ataaaaaagg caatatcttt   1380
tctcatcaag gcagaatcag ttgtcatttt ctggatttct ttactcgaca aaccaaaggc   1440
aaacatcctc ttggtgatct tgcaagtcat caggaagctc tccaggaagg aacctccaat   1500
cgcttacatc acaagaatga ggtagtagcc caggggtacg aaaaactgga tcaattcaag   1560
aaagaggttg tcaaactgct ggctgagaat aaaccaaaag aattattgga ttatttggtt   1620
gctacctcac ctacaggtgt tccaaattac tccatgcttt cgaaggaaac tcaaaattac   1680
attgcttata atcgtaactg gccagccatt caaaaagagc tggaaaaggc taccagcatc   1740
ccggagagtc aaaaacaaga tctttcaaga ttgctttctc gtgataattt acaacacgat   1800
aatctaagcg caattacctg gtcaaaatat tcctccaagc cattattgga tgtggaatta   1860
aataaaatcg ctgaaggatt agaactcact gcaaaaattt acaatgaaaa gagaggacgc   1920
gaatggtggt ttaaaggttc aagaaatgaa gctcgtaaga cccaatgtga agaattgcaa   1980
agagtatcca aagaaatcaa tactcttctg caaagtgaat ctttaacgaa aagccaggta   2040
cttgaaaagg ttttaaattc tatagaaaca ttagataaaa ttgacagaga catttctgcc   2100
gaatccaatt ggtttcaaag tactctgcaa aaggaagtca ggttatttcg agatcaattg   2160
aaagatattt gccaattgga caagtatgcc tttaaatcaa caaaacttga tgaaatcatc   2220
tctctggaaa tggaagaaca atttcaaaag atacaagatc ctgctgttca acaaattgtc   2280
agggacttgc cttctcattg ccacaatgat gaagcaattg aattctttaa gacattgaac   2340
cctgaagagg cagcaaaagt agctagctat ttaagcctgg aatacaggga aattaataaa   2400
tcaaccgata agaaaactct cctagaacaa gatattccca gactgtttaa agaagtcaat   2460
acgcagttac tctccaaact caaagaagaa aaagctattg atgagcaagt tcatgaaaaa   2520
ctcagtcaac tggctgacaa aattgcccct gagcatttta caagaaataa cattataaaa   2580
tggtctacca accctgaaaa gcttgaggaa tcaaatctta atgagccaat caaatcagtc   2640
caaagcccta ctactaaaca aacatcaaaa caattcaggg aagcgatggg tgaaatcact   2700
ggaagaaatg agcctcctac agacactttg tacacgggaa ttataaagaa atag          2754
```

<210> SEQ ID NO 4
<211> LENGTH: 2727
<212> TYPE: DNA
<213> ORGANISM: L. pneumophila

<400> SEQUENCE: 4

```
gtgatgaaca tggttgacaa aataaaattc aaagagccgg agcgatgcga atatttacat     60
atcgctaagg ataataaagt ccatattctt ttacctattg taggtgggga tgaaatagga    120
ctggataata cctgtgaaac aacaggtgag ttattaacct ttttctatgg aaaaacgcat    180
ggtgggacaa agtattctgc tgaacatcac ctaaatgaat ataaaaagaa tctggaagat    240
gatataaagg caatcggtgt tcaaagaaaa atttcaccaa atgcctatga agatctatta    300
aaagagaaaa aagagcgcct ggaacaaatc gaaaaatata ttgatttaat caaagtactc    360
```

```
aaagagaaat tgatgagca aagagaaata gacaaactac gcacagaagg aatcccgcaa      420
ttaccttctg gagtaaagga agtcattaaa tcttctgaaa atgcctttgc tttaaggctt      480
tccccggata gaccagactc atttacccgc tttgatgatc ctctgtttag tctcaaaaga      540
aacagatctc aatatgaagc tgggggatac caacgggcaa ctgatggatt aggggctcgt      600
ttgcgttctg agcttctacc accagataaa gacactccta ttgtttttaa taaaaaatca      660
ctgaaggaca aaatcgtaga ttctgtttta gtgcaacttg acaaagattt taatacaaaa      720
gatggcgatc gtggtcaaaa atttgaggat ataaaaaaac tcgttctaga agagtacaag      780
aaaattgatt ccgaacttca agtggatgag gataccctatc accaaccact taacttggat      840
tatttggaaa acatagcatg tacgttagat gacaactcca ccgcgaaaga ttgggtttat      900
ggaattattg gtgctacaac agaagctgat tattggccaa aaaaggaaag tgaaagtggt      960
actgaaaaag ttagtgtatt ctatgagaag caaaaggaaa taaaatttga atctgataca     1020
aatacaatgt caattaaagt ccaatatcta ttagctgaga ttaattttta ttgtaaaacc     1080
aacaagttat cagatgctaa cttcggtgaa ttttttgata agagccccca tgctactgaa     1140
gttgctaaaa gagtgaaaga aggacttgtt caaggagcag agattgagcc tattatttac     1200
aattacatta acagccacca tgccgaactg ggattaacat ctgagttaag cagcaagcaa     1260
caagaggaaa ttactgaaaa atttactcaa cgttatcaca ttattgagaa ctctcctcac     1320
tttgatgaat tttttgtcgc tgatcctgat aaaaaaggga atatattctc ccatcaaggc     1380
agaatgagtt gccatttcct ggatttcttc gctcgacaaa ccaaaggcaa atatcccctt     1440
ggtgatcttg caggtcatca agaagcactc caggcaggaa cttccaatcg gttacatcac     1500
aagaatgagg tagtcgctca aggatatgaa aaatttgatc aattcaagaa agaagtcgtc     1560
aaactgctgg cagagagtaa accaaaagaa ttattggatt atttggttgc tacctccccc     1620
acaggtgttc ctaattattc catgctctca aaggaaactc aaaattatat tgcttacaac     1680
cgtaactggc cagccattca aaaagagctc gaaaaaacta ctgacatacc agagaaccaa     1740
aaacaagatc ttttaagatt gctttctcgt aataatctgc aacacgagaa cctcagtgca     1800
attacctggt caaaatactc ttccaagcca ttattggatg tggagttaaa taaaatcgcc     1860
gaaggtttag atctaactgc taaaatttac aatgaaaaaa gaaaaagtga atggtttaaa     1920
ggttcaagaa atgaggctcg taagacccaa tgtgaagaat tgcaaagagt atcccaagaa     1980
atcaatgctc ttctgcaaag tgaatcttta acaaaaagcc aagttcttga aaagttttta     2040
aactccatag aagcattgga taaaattgat agagacattt ctgctgaata taatttattt     2100
aagagtactc tgcaaaaaga agtacaatca tttcgagatc aattgaagga tatctgtcaa     2160
ttagataact atgcctttaa atcaacaaaa cttgatgaaa ttatctctct ggaaatggaa     2220
gaacaatttc aaatgattaa agatcctgct gtccaacaaa ttgtccgaga cttgccttct     2280
cattgtcata taatgaagt gattgaattc tttatgacat taaatcctga agaagcagct     2340
aaagtagcta gctatttaag cctcgagtac cgggaactca ataaatcaac agataagaaa     2400
actctccttg aacaagatat tcctaaatta tttaaagaag tgaatatgga actattatcc     2460
caattaaaac aagatagtgc agttaaggaa gacgtctatg aaaaattctg tcaattagct     2520
gataaaattc ctcctgagca ttttacaagg aataatatca ggaaatggtc tgccaatcct     2580
gaaaaacttg aggagtccaa tctcggtgaa ttactaaaat cctctgaagg ctcaattact     2640
gaaatggcaa gaaaatacag agaaaccata aatgaaatga caggaagaaa tgagtcactc     2700
agagaaactg ttaggaatac aatatag                                        2727
```

<210> SEQ ID NO 5
<211> LENGTH: 1151
<212> TYPE: PRT
<213> ORGANISM: L. pneumophila

<400> SEQUENCE: 5

```
Met Asn Glu Ile Ile Leu His Leu Met Asn Glu Ile Ser Thr Leu Thr
1               5                   10                  15

Pro Pro Ile Asn Pro Leu Asn Leu Lys Gln Ile Phe Ser Ser Thr Leu
            20                  25                  30

Leu Pro Glu Gly Lys Ala Pro Val Glu Val Glu Ser Gln Leu Asn Leu
        35                  40                  45

Leu Leu Leu Ile Lys Lys Tyr Val Asp Glu Tyr Ser Ser Leu Ala Glu
    50                  55                  60

Glu Gln Glu Glu Tyr Lys Arg Lys Lys His Lys Leu Asp Glu Val Met
65                  70                  75                  80

Lys Lys Gly Glu Glu Leu Gln Arg Lys Ile Ser Asp Leu Ala Lys Lys
                85                  90                  95

Ile Glu His Ala Lys Asn Glu Leu Asn Pro Leu Tyr Lys Glu Ile Glu
            100                 105                 110

Pro Lys Ala Asn Glu Val Leu Ser Lys Gln Asn Pro Leu Ala Pro Pro
        115                 120                 125

Tyr Lys Phe Pro Glu Tyr Gly Glu Val Gln Lys Ser Ile Val Val Gly
    130                 135                 140

His Tyr Ser Tyr Leu Phe Lys Thr Ser Lys Glu Ile Glu Thr Thr Arg
145                 150                 155                 160

Ala Lys Leu Lys Leu Val Leu Leu Lys Asn Lys Trp Asn Ala Leu Met
                165                 170                 175

Ala Asp Leu Ser Gln Phe Gly Ile Gln Pro Pro Val Glu Glu Asp Ala
            180                 185                 190

Val Asp Ser Leu Gln Lys Phe Ile Ala Ala Val Glu Leu Glu Ile Lys
        195                 200                 205

Lys Leu Thr Arg Ala Cys Glu Lys Trp Asp Glu Leu Gln Lys Arg Phe
    210                 215                 220

Ala Lys Gln Leu Ser Ala Thr Asp Ile Asn Lys Lys Glu Ser Glu Leu
225                 230                 235                 240

Glu Lys Gln Ile Glu Leu Leu Leu Lys Asp Val Gly Arg Ile Glu Thr
                245                 250                 255

Val Val Thr Asn His Ser Leu Ala Pro Asp Leu Lys Ala Glu Leu Thr
            260                 265                 270

Arg Lys Phe Gln Glu Ser Glu Asp Thr Gln Gly Leu Ile Gln Glu Tyr
        275                 280                 285

Gln Asn Gln Ile Asp Gly Leu Leu Ser Asn Phe Asn Pro Ser Ser Trp
    290                 295                 300

Leu Ser Trp Tyr Ser Asp Ser Asn Tyr Ser Asp Asn Gln Gln Lys Leu
305                 310                 315                 320

Lys Asn Ser Val Ser Phe Leu Gln Leu Leu Ala Gln Gln Lys Glu Leu
                325                 330                 335

Lys Ile Lys His His Glu Leu Val Lys Gln Gln Glu Leu Leu Ile Lys
            340                 345                 350

Ala Ile Pro Glu Thr Pro Ser Asn Glu Glu Asp Ile Ser Ile Tyr Lys
        355                 360                 365

Lys Leu Val Pro Asp Ala Ile Asp Leu Ile Asn Glu Ile Pro Ile Glu
```

-continued

```
                370              375             380
Ser Ile Pro Asn Phe Val Leu Pro Ser Gly Leu Ser Tyr Asp Ser Ser
385                 390                 395                 400

Pro Ala Asp Phe Tyr Leu Val Leu Leu Ile Leu Met Pro Lys Val Ser
                405                 410                 415

Glu Lys Lys Glu Gln Phe Ser Gln Ala Leu Glu Lys Leu Gln Glu Met
                420                 425                 430

Pro Ala Leu Gly Lys Gln Ile Gln Gln Leu Arg Ser Gly Tyr Asp Leu
                435                 440                 445

Pro Ile Thr Met Asp Val Gln Leu Pro Ser Leu Gln Glu Ala Glu Glu
                450                 455                 460

Ser Lys Asp Ser Leu Asn Glu Glu Asp Pro Leu Lys Glu Glu Leu Lys
465                 470                 475                 480

Ser Gln Ile Lys Leu Cys Gln Ser Tyr Leu Glu Thr Ala Lys Gln Ile
                485                 490                 495

Asp Leu Leu Met Lys Asp His Gly Gln Thr Thr Asn Glu Ala Lys Ala
                500                 505                 510

Leu Ile Glu Gln Leu Arg Leu Ile Ser Asn Gln Pro Leu Lys Asn Glu
                515                 520                 525

Asp Ile Asn Ser Ile Lys Glu Asp Leu Ser Thr Leu Ala Asn Gln Ile
                530                 535                 540

Gln Ser Leu Val Ser Glu Leu Asn Gln Leu Pro Leu Pro Asn Leu Ser
545                 550                 555                 560

Gly Glu Lys Ile Asp Pro Pro Leu Glu Lys Gln Glu Ile Ala Val Asp
                565                 570                 575

Lys Thr Ile Pro Leu Thr Val Glu Leu Met His Pro Ala Gln Val Ile
                580                 585                 590

Gln Ile Gly Asn Asp Ser Pro Ile Glu Lys Gln Gln Leu Asp Asn Glu
                595                 600                 605

Glu Glu Thr Pro Val Val Leu Glu Ser Leu Arg Pro Arg Pro Val Ile
                610                 615                 620

His Lys Glu Ser Glu Ser Ile Thr Gln Lys Leu Gln Val Asp Asn Gly
625                 630                 635                 640

Gln Glu Met Pro Val Val Leu Asp Ser Thr Cys Thr Pro Gln Ala Ile
                645                 650                 655

His Lys Glu Leu Glu Ser Thr Thr Glu Lys Leu Gln Val Asp Asn Gly
                660                 665                 670

His Glu Ile Pro Val Val Leu Glu Ser Thr Arg Ser Pro Gln Ile Ile
                675                 680                 685

His Thr Glu Ser Glu Ser Val Gly Lys Lys Gln His Val Glu Val Glu
                690                 695                 700

Gln Glu Ile Pro Val Thr Leu Glu Leu Ile Arg Pro Ser Ser Met Val
705                 710                 715                 720

Glu Lys Asp Ser Val Ala Thr Val Glu Lys Gln Val Thr Glu Arg
                725                 730                 735

Gln Glu Thr Pro Ile Val Leu Glu Ser Thr Arg Leu Ser Pro Met Val
                740                 745                 750

Gln Lys Asp Thr Gly Leu Ser Gly Glu Lys Gln His Lys Glu Ile Glu
                755                 760                 765

Gln Glu Ile Ser Val Val Thr Glu Leu Thr Pro His Thr Gln Val Val
                770                 775                 780

Arg Gln Gly Ser Glu Ser Ser Leu Glu Gln Gln Val Pro Asn Gly Gln
785                 790                 795                 800
```

-continued

```
Glu Thr Leu Ala Val Val Lys Ser Ser Pro Ser Glu Pro Leu Arg Pro
                805                 810                 815

Ser Thr Pro Glu Val Pro Ala Ile Ser Arg Lys Pro Asn Gly Leu Ser
            820                 825                 830

Leu Phe Asn Gly His Asp Glu Leu Ser Glu Asp Asn Ile Leu Ala Phe
        835                 840                 845

Phe Asp Glu Ala Gly Asn Gln Ile Ser Ile Ser Ser Glu Glu Asp Ser
    850                 855                 860

Glu Thr Phe Thr Val Asp Arg Gly Lys Val Ile Ser Ser Gly Ile Asp
865                 870                 875                 880

Lys Ala Phe Lys Glu Lys Pro Val Ser Thr Gly His Glu Leu Asp Lys
                885                 890                 895

Leu Ser Asn Pro Gln His Gln Glu Ser Ala Pro Ser Ile Ser Pro Leu
            900                 905                 910

Pro Pro Ser Ser Ile Leu Leu Lys Gln Lys Leu Asp Ser Phe His Val
        915                 920                 925

Gln Asn Met Glu Tyr Ile Lys Gln His Ser Glu Glu Ile Gln Leu Trp
    930                 935                 940

Tyr Lys Gly Leu Tyr Asp Ala Ala Gln Ser Ser Cys Val Asn Glu Ala
945                 950                 955                 960

Leu Gly Leu Lys Ala Leu His Leu Leu Lys Asp Ile Leu Phe Glu Leu
                965                 970                 975

Lys Asn Gln Asn Asp Leu Ser Val Leu Leu Ala Tyr Lys Arg Met Cys
            980                 985                 990

Pro Asn Pro Leu Gln Asp Ile Gln Asn Ile Leu Arg Leu Lys Pro Ala
        995                 1000                1005

Leu Pro Ile Val Asp Glu Ser Ile Asp Glu Glu Gln Gln Leu Lys Asn
    1010                1015                1020

Trp Pro Glu Glu Leu Gln Lys Phe His Gln Gln Tyr Val Lys Leu Lys
1025                1030                1035                1040

Lys Glu His Pro Leu Glu Ala Glu Leu Phe Ile Gln Ala Ile His Ser
                1045                1050                1055

Leu Ile Ser Ile Lys His Leu Met Glu Leu Pro Asp Ala Lys Thr Ser
            1060                1065                1070

Asn Arg Glu Ala Met Pro Leu Ile Thr Gln Asp Pro Arg Tyr Glu Pro
        1075                1080                1085

Leu Lys Arg His Arg Gly Phe Ile Arg Ala Trp Glu Tyr Ile Glu Asp
    1090                1095                1100

Phe Phe Arg Met Leu Ile Gly Lys Leu Thr Gly Gln Asp Glu Tyr Glu
1105                1110                1115                1120

Tyr Ser Lys Arg Pro Cys Phe Phe Lys Thr Arg Ser His Arg Leu Leu
                1125                1130                1135

Glu Glu Val Asp Thr Ile Leu His Ser Met Ala Pro Thr Ser Ser
            1140                1145                1150

<210> SEQ ID NO 6
<211> LENGTH: 1294
<212> TYPE: PRT
<213> ORGANISM: L. pneumophila

<400> SEQUENCE: 6

Met Leu Ile Tyr Gln Gly Lys Glu Ile Val Arg Phe Lys Glu Lys Thr
1               5                   10                  15

Gly Gly Lys Asn Lys Ser Asp Val Asp Gly Phe Tyr Lys Asp Asn Asp
```

```
                 20              25              30
Gly Gly Lys Phe Phe Ile Lys Lys Pro Gly Asp Pro Arg Glu Leu Phe
            35                  40                  45

Thr Glu Leu Phe Ala Gly Leu Leu Lys Glu Phe Met Lys Arg Gly
    50                  55                  60

Leu Ile Asp Glu Ser Tyr Phe Pro Ser Leu Ile Cys Ala Asp Val Ile
65              70                  75                  80

Gln Phe Glu Asp Lys Ser Tyr Gly Leu Ile Gln Pro Leu Val Ser Phe
                85                  90                  95

Asp Glu Leu His Lys Val Ile Gly Thr Ser Gly Asp Gly Lys Asp
                100                 105                 110

Arg Asn Thr Leu Lys Glu Thr Leu Phe Gly Pro Gly Tyr Tyr Ala Gly
            115                 120                 125

Ile Thr Lys Gln Asn Lys Tyr Phe Gly Leu Ser Met Ala Leu Met Phe
            130                 135                 140

Ser Leu Leu Leu Gly Ala His Ser Val His Ser Gly Asn Ile Val Val
145                 150                 155                 160

Leu Asn Gly Glu Glu Lys Glu Lys Ser Lys Gln Phe Gly Arg Ile Asp
                165                 170                 175

Trp Gly Asp Ala Phe Arg Tyr Phe Ala His Pro Asn Asn Asp Asn
            180                 185                 190

Leu Leu Tyr Ala Tyr Glu Asn Arg Gly Trp Phe Asn Tyr Lys Ser Leu
            195                 200                 205

Thr Lys Asp Tyr Phe Leu Asn Tyr Lys Lys Ile Asn Gly Leu Phe Pro
    210                 215                 220

Ala Met Ala Glu Lys Ala Arg Gln Leu Gln Ser Lys Leu Asn Pro Glu
225                 230                 235                 240

Leu Leu Val Lys Ile Val Thr Ser Ala Leu Lys Asn Ile Pro Ala Asp
                245                 250                 255

Leu Ile Asp Glu Lys Thr Lys Ile Gln Leu Ala Ala Tyr Met Cys Met
            260                 265                 270

Asp Ser Phe Lys Glu Ala Thr Phe Gly Thr Glu Gly Asn Cys Lys Asp
            275                 280                 285

Phe Ala Ile Ala Met Ala Thr Leu Leu Glu Asn Arg Leu Gly Lys Ile
    290                 295                 300

Ala Val Leu Lys Asp Met Ser Pro Leu Ser Asn Pro Glu Glu Leu Tyr
305                 310                 315                 320

Gln Ser Ile Leu Glu Leu Lys Pro Leu Thr Leu Leu Met Thr Ser Ser
            325                 330                 335

Thr Ser Phe Ser Glu Thr Ile Asn Gln Trp Ala Asp Ile Leu Lys Thr
            340                 345                 350

Thr Asp Met Glu Lys Phe Ser Phe Asp Ser Asn Pro Ile Asn Leu Leu
    355                 360                 365

Glu Leu Val Lys Gln Phe Asn Leu Tyr Val Asp Glu Leu Ala Ile Thr
            370                 375                 380

Cys Glu Ala Asn Asn Val Trp Ala Lys Glu Arg Ile Asp Ser Thr Pro
385                 390                 395                 400

Asn Leu Phe Ala Leu Tyr Asp Asn Ser Gly Gly Glu Ala Ile His Gly
            405                 410                 415

His Ala Phe Val Pro Tyr Tyr Lys Glu Ser Ile Val Leu Arg Arg Leu
            420                 425                 430

Phe Thr Val Asp Pro Asn Thr Phe Asn Leu Ser Arg Phe Ala Ala Phe
            435                 440                 445
```

-continued

```
Glu Gly Pro Cys Gln Leu Tyr Cys Lys Glu His Lys Asp Ser Ala Trp
        450                 455                 460
Val Lys Ile Gln Thr Leu Leu Thr Leu Gly Asn Gly Ile Ile Asn Thr
465                 470                 475                 480
Leu Lys Ile Ile Lys Gln Ala Gln Ala Phe Gly Ile Asp Glu Ala Val
                485                 490                 495
Thr Glu Asn Leu Lys Ala Leu Lys Glu Gln Phe Ile Ala Phe Gln Leu
            500                 505                 510
Ala Glu Ala Asp Ile Lys Glu Ser Leu Lys Ala Pro Ser Phe Ala Glu
        515                 520                 525
Pro Leu Pro Asn Lys Glu Ser Glu Phe Phe Tyr Pro Ile Asp Glu Lys
    530                 535                 540
Ala Leu Ala Lys Met Asn Gly Tyr Gln Leu Ala Thr Ile Cys Leu Glu
545                 550                 555                 560
Glu Leu Asn Ser Pro Lys Pro Ser Pro Leu Ile Glu Arg Ile Leu Ser
                565                 570                 575
Asn Lys Lys Phe Trp Lys Arg Ile Asn Ser Ala Phe Glu Ser Gly Val
            580                 585                 590
Phe Lys Gly Arg Thr Asp Asp Pro Ala Gly Lys Ile Ala Lys Ile Arg
        595                 600                 605
Glu Trp His Gln Leu Leu Gln Ile Ser Gly Lys Lys Thr Ala Gly Gln
    610                 615                 620
Ile Asp Glu Leu Gln Lys Ile Val Ile Ser Leu Gln Ser Lys Ile Lys
625                 630                 635                 640
Arg Gln Thr Ile Glu Phe Glu Leu Glu Ala Thr Leu Ile Gln Ile
                645                 650                 655
Lys Glu Lys Tyr Gln Leu Leu Glu Lys Met Ala Glu Gln Ser Glu His
            660                 665                 670
Glu Lys Ser Ser Ala Gln Ser Ile Ile Arg Ser Leu Asn Leu Glu Leu
        675                 680                 685
Ser Gln Leu Lys Leu Gln Leu Gln Glu Gln Glu Lys Leu Gln Phe Gln
    690                 695                 700
Leu Lys Glu Leu Lys Glu Lys Ile His Glu Gln Thr Thr Leu Ser Lys
705                 710                 715                 720
Arg Leu Gly Glu Glu Leu Gln Thr Gln Lys Lys Thr Asn Thr His Gln
                725                 730                 735
Glu Glu Thr Ile Gln Arg Ile Thr Lys Glu Lys Ser Leu Ala Asp Ser
            740                 745                 750
Ser Leu Glu Ser Leu Arg Lys Glu Leu His Glu Leu Ala Lys Lys Glu
        755                 760                 765
Arg Ser Leu His Lys Thr Leu Glu Glu Lys Gln Leu Gln Val Gln Gln
    770                 775                 780
Leu Glu Glu Gln Leu Ala Glu Lys Glu Glu Asn Leu Ala Leu Lys
785                 790                 795                 800
Lys Ala Asp Lys Gln Ser Gln His Glu Lys Ser Leu Asp Lys Ser Ala
                805                 810                 815
Ile Glu Ser Leu Thr Ser Glu Leu Asn Gln Leu Lys Leu Glu Leu Gln
            820                 825                 830
Lys Gln Glu Thr Leu Gln Leu Gln Leu Lys Ser Leu Arg Lys Gln Ile
        835                 840                 845
Gln Glu Gln Thr Leu Val Val Glu Gly Leu Lys Glu Glu Leu Gln Lys
    850                 855                 860
```

-continued

```
Gln Lys Lys Ser Asn Thr His Gln Glu Glu Thr Ile Glu Arg Ile Thr
865                 870                 875
Lys Glu Lys Ser Leu Ala Asp Ser Ala Leu Glu Ser Leu Arg Lys Glu
880                 885                 890   895
Met Tyr Glu Leu Thr Arg Lys Asn Glu Glu Asn Gln Leu Lys Leu Thr
                900                 905                 910
Lys Gln Val His Ser Leu Ser Glu Gln Leu Glu Glu Lys Gln Leu Gln
                915                 920                 925
Ile Arg Glu Phe Glu Lys Gln Leu Gln Glu Lys Glu Lys Arg Val Glu
            930                 935                 940
Gln Ser Glu Lys Gly Lys Ala Ser Ala Lys Arg Thr Val Ala Ser Leu
945                 950                 955
Arg Glu Gln Val Ser Asn Leu Lys Leu Gln Leu Gln Gln Leu Gly Glu
960                 965                 970   975
Val Ile Gln Glu Lys Glu Lys Gly Ser Ser Leu Ile Ser Gln Gln Ser
                980                 985                 990
Lys Gln Ile Ile Ala Leu Gln Glu Ile Ile Glu Asp Gln Lys Arg Gln
                995                 1000                1005
Leu Glu Glu Leu Lys Ile Lys Ile Gln Glu Leu Val Ser Ala Asn Gln
            1010                1015                1020
Glu Leu Gly Lys Gln Asn Gln Ser Leu Ser Lys Glu Asn Leu His Asn
            1025                1030                1035
Lys Asn Thr Val Glu Asp Leu Lys Lys Leu Asn Glu Leu Asn Val
1040                1045                1050   1055
Gln Leu Glu Gln Leu His Gln Ser Ser Asn Glu Lys Glu Gln Thr Ile
                1060                1065                1070
Arg Lys Leu Arg Glu Glu Leu Ile Lys Lys Asp Ser Ser Leu Lys Gln
            1075                1080                1085
Asn Glu Glu Met Gln Leu Ala Gln Lys His Leu Gln Glu Glu Ile Asp
            1090                1095                1100
Arg Leu Gln Lys Glu Ile Lys Gln Gln Gln Leu Asn Thr Asn Gln Leu
            1105                1110                1115
Glu Ser Ile Ile Ala Gln Ser Lys Glu Ala Glu Lys Arg Tyr Gln Gln
1120                1125                1130   1135
Ala Leu Gln Gln Lys Lys Gly Ile Tyr Phe Ala Arg Met Glu Arg Val
                1140                1145                1150
Ser Pro Ile Tyr Leu Gln Ile Gln Gln Ile Glu Gln Lys Ala Lys Glu
                1155                1160                1165
Leu Glu Glu Arg Arg Glu Thr Glu Ala Ser Thr Ala Ala Lys Thr Leu
            1170                1175                1180
Ala Thr Lys Leu Arg Leu Glu Ile Lys Asn Tyr Leu Asp Asn Asn Glu
1185                1190                1195
Ser Asp Glu Lys Ser Ala Leu Asn Ser Phe Lys Ile Asn Ala Lys Arg
1200                1205                1210   1215
His Ile Glu Asn Ser Lys Glu Thr Leu Asn Gln His Arg Glu Glu Trp
                1220                1225                1230
Lys Tyr Leu Leu Ala Asn Val Thr Leu Gly Val Phe Leu Leu Gly Ile
                1235                1240                1245
Gly Tyr Leu Ala Ala Ile Leu Ile Asn Lys Ala Thr Thr Gly Asn Tyr
            1250                1255                1260
Thr Phe Phe Ser Gln Thr Asn Ser Gly Lys Lys Leu Asp Ala Leu Glu
            1265                1270                1275
Lys Ala Ile Ser Ser Thr His Ser Glu Thr Leu Val Tyr Gly
```

-continued 1280 12851290

<210> SEQ ID NO 7
<211> LENGTH: 113
<212> TYPE: PRT
<213> ORGANISM: L. pneumophila

<400> SEQUENCE: 7

```
Ala Gln Met Ala Leu Gln Arg Asn Ile Asn Leu Gln Asn Gln Gln Asp
1               5                   10                  15

Arg Met Glu His Glu Leu Phe Lys Arg Arg Leu Met Ala Ala Leu Phe
            20                  25                  30

Leu Trp Tyr Leu Ser Lys Lys Ser His Ala Ala Glu Lys Val Lys Glu
        35                  40                  45

Ile Ile Arg Glu Tyr Asn Glu Lys Ala Ile Lys Asn Ala Glu Lys Ala
    50                  55                  60

Ser Lys Pro Ser Gln Gln Ser Thr Ser Ser Thr Ser Gln Ala Asp Lys
65                  70                  75                  80

Glu Ile Gln Lys Met Leu Asp Glu Tyr Glu Gln Ala Ile Lys Arg Ala
                85                  90                  95

Gln Glu Asn Ile Lys Lys Gly Glu Glu Leu Glu Lys Lys Leu Asp Lys
            100                 105                 110

Leu
```

<210> SEQ ID NO 8
<211> LENGTH: 1167
<212> TYPE: PRT
<213> ORGANISM: L. pneumophila

<400> SEQUENCE: 8

```
Met Ile Leu Glu Glu Tyr Ile Arg Met Ala Lys Asn Lys Glu Phe Phe
1               5                   10                  15

Asp Ala Leu Glu Glu Ile Ala Glu Ser Ala Lys Asn Asp Glu Thr Leu
            20                  25                  30

Arg Asn Glu Leu Ala Lys Val Leu Asp Asp Ile Leu Lys Thr Asp Pro
        35                  40                  45

Ser Asp Pro Glu Ala Phe Arg Lys Ile Val Ala Glu His Gln Glu Phe
    50                  55                  60

Trp Asp Glu His Asp Pro Ser Leu Met Glu Phe Asn Glu Gly Arg Phe
65                  70                  75                  80

Phe Gly Lys Ser Arg Lys Gln Tyr Leu Lys Ser Asp Asp Phe Leu Asn
                85                  90                  95

Ser Thr Asp Pro Thr Tyr Asn Phe Gln Lys Leu His Gln Phe Ala Ala
            100                 105                 110

Glu Gln Arg Val Lys Leu Gly Leu Glu Lys Ser Asp Thr Asp Thr Leu
        115                 120                 125

Val Ala Ile Leu Lys Asn Asn Pro Glu Glu Cys Arg Ala Tyr Ile Glu
    130                 135                 140

Ser Lys Lys Pro Gly Leu Gly Asn Phe Ser Glu Gly Asn Val His Gly
145                 150                 155                 160

Trp Leu Lys Glu Glu Tyr Thr Pro Thr Ile Pro Pro Lys Ala Ile Asn
                165                 170                 175

Lys Ser Thr Gly Val Leu Ser Asp Glu Ala Ile Lys Arg Ile Lys Glu
            180                 185                 190

Gln Ala Arg Asp Leu Leu Leu Leu Lys Leu Ile Asn Ser Ser Gly Asn
        195                 200                 205
```

-continued

```
Thr Gln Leu Leu Lys Asp Leu Arg Asp Ala Met Ser Lys Pro Glu Ala
    210                 215                 220
Glu Arg Ala Ala Asn Ala Leu Gly Phe Pro Thr Gly Asn Gly Val
225                 230                 235                 240
Leu Phe Leu Ser Arg Glu Val Val Asp Ala Leu Glu Glu Arg Val Glu
                245                 250                 255
Lys Leu Glu Gln Glu Ala Ala Lys Arg Gly Phe Asp Ser Tyr Val Gln
                260                 265                 270
Ser Leu Ser His Asn Ala Leu Leu Ala Lys Lys Asn Gly Leu Glu Ser
            275                 280                 285
Thr Thr Ala Ala Gly Phe Lys Asn Ser Leu Asp Glu Pro Tyr Lys Thr
    290                 295                 300
Tyr Leu Pro Glu Ser Glu Trp Glu Arg Ala Gln Gly Val Leu Gly Ala
305                 310                 315                 320
Arg Tyr Leu Gln Ala Val Leu Ser Ser Gly Thr Gln Asn Leu Lys Asp
                325                 330                 335
Ala Leu Asn Ala Lys Asp Ala Asn Ala Leu Ile Thr Glu Leu Lys Lys
            340                 345                 350
Pro Ala Leu Leu Gly Pro His Asp Tyr Ile Asp Lys Ala Val Thr Glu
            355                 360                 365
Glu Asn Leu Gly Ser Leu Lys Lys Asn Met Met Lys Ser Phe Ile Asn
    370                 375                 380
Asn Ile Lys Asp Glu Thr Asn Leu Lys Ala Leu Asp Ala Leu Lys Ala
385                 390                 395                 400
Leu Asp Gly Ala Lys Asn Leu Asp Lys Phe Lys Glu Val Leu Gly Lys
                405                 410                 415
Leu Gly Ile Thr Pro Ala Asp Trp Lys Asp Thr Asp Leu Lys Asp
                420                 425                 430
Met Lys Gln Trp Ala Arg Ala Arg Gln Phe Glu Leu Glu Ile Asn Arg
            435                 440                 445
Val Ser Ser Leu Gly Ser Gly Ala His Ser Lys Leu Met Ser Thr Leu
    450                 455                 460
Thr Lys Leu Pro Val Glu Lys Gln Arg Glu Ile Leu Ala Lys Pro Gln
465                 470                 475                 480
Gln Leu Arg His Leu Met Asn Ala Tyr Glu Ser His Val Ala Glu His
                485                 490                 495
Tyr Leu Gly Lys Asn Ala Ser Gly Ile Ala Glu Leu Leu Thr Glu Asn
                500                 505                 510
Lys Arg Leu Glu Gly Phe Arg Ala Ile His Asn Ala Glu Val Ala Arg
            515                 520                 525
Val Leu Ala Asn Phe Lys Pro Glu Ile Thr Leu Asn Asp Lys Gln Val
    530                 535                 540
Ala Ala Ile Asn Gln Ala Leu Thr Thr Ala Asn Ser Asn Pro Asn Thr
545                 550                 555                 560
Tyr Thr Gln Ala Thr Asp Tyr Lys Ile Leu Ile Asp Ala Ile Lys Thr
                565                 570                 575
Gln Ser Gly Ser Val Asn Gln Lys Asp Phe Tyr Asn Ala Phe Asn Leu
            580                 585                 590
Asn Asp Asp Gly Arg Ala Phe Thr Ser Thr Pro Arg Lys Asp Glu
            595                 600                 605
Met Ser Lys Gln Gln His Asn Gln His Ile Tyr Ala Glu Tyr Asn
    610                 615                 620
```

```
Ser Thr Ser Asn Ser Gly Asn Lys Lys Leu Leu Ala Val Leu Leu Ser
625                 630                 635                 640

Ile Glu Lys Pro Val Thr Phe Ser Lys Asp Ile Val Asn Arg Phe Leu
            645                 650                 655

Arg Pro Leu Lys Asp Ser Glu Thr Pro Gln Asp Tyr Ala Asp Thr Leu
        660                 665                 670

Phe Gly Glu Asn Pro Thr Asn Pro Ala Asn Lys Lys Phe Lys Asp Asp
    675                 680                 685

Leu Leu Arg Glu Leu Thr Pro Thr Val Phe Asn Glu Ile Lys Asn Asp
690                 695                 700

Leu Arg Lys Gln Glu Leu Leu Asp Thr Asn Pro Ala His Val Met Thr
705                 710                 715                 720

Ala Ile Lys Ala Leu Ser Thr Glu Leu Glu Ser Ile Lys Gly Ile Thr
                725                 730                 735

Gly Pro Ile Arg Thr Asn Ala Asp Lys Leu Lys Phe Ile Asn Asp Ile
            740                 745                 750

Asp Pro Val His Leu Tyr Asn Pro Thr Phe Gln Gly Thr Ala Arg Ser
        755                 760                 765

Lys Ala Ala Gln Met Lys Glu Arg Tyr Glu Gly Leu Ser Arg Asp Cys
770                 775                 780

Gly Leu Val Val Asp Gln Leu Arg Arg Gln Val Val Ala Leu Glu Gly
785                 790                 795                 800

His Leu Lys Ser Leu Pro Lys Glu Gly Glu Phe Lys Ala Ala Gly Leu
                805                 810                 815

Thr Leu Glu Gln Lys Ala Glu Ile Lys Lys Leu Arg Thr Asp Leu Glu
            820                 825                 830

Ala Glu Leu Ser Ala Val Arg Glu Asp Leu Asp Phe Tyr Lys Lys Ile
        835                 840                 845

Gln Gly Lys Leu Glu Thr Ile Val Lys Glu Val Asp Val Ala Ala Lys
850                 855                 860

Gly Lys Met His Tyr Tyr Tyr Asn Ser Glu Gly Ile Lys Arg His Pro
865                 870                 875                 880

Pro Val Ser Arg Asp Gln Ile Pro Pro Leu Pro Asn Val Pro Asn Pro
                885                 890                 895

Ser Leu Arg Ser Ser Thr Thr Ala Thr Thr Gly Ser Asn Gly Arg Ile
            900                 905                 910

Gln Glu Phe Leu Val Gly Glu Lys Ile Pro Glu Gly Gln Ile Val Val
        915                 920                 925

Val Asp Val Ser His Lys Thr Ala Pro Lys Ser Gly Ala Pro Val Glu
930                 935                 940

Thr Ile Gly Arg Tyr Thr Gln Asp Asn Val Pro Asp Gln Val Thr
945                 950                 955                 960

Ser Lys Lys Gly Glu Ile Ser Lys Val Pro Gly Ser Lys Phe Glu Ile
                965                 970                 975

Leu Gln Phe Pro Thr Gln Val Pro Pro Asn Pro Ser Gly Asp
            980                 985                 990

Pro Leu Val Glu Ala Lys Val Asn Phe Ser Met Ala Met Ala Ala Asp
        995                 1000                1005

Ile Leu Ala Ser Leu Asp Ser Pro Thr Lys Asp Lys Pro Ile Arg
        1010                1015                1020

Leu Arg Gly Ser Asn Pro Glu Glu Leu Glu Tyr Leu Tyr Thr Ala Leu
1025                1030                1035                1040

Val Ile Leu Gly Glu Lys Asn Pro Lys Phe Lys Phe Asn Arg Asp Ala
```

-continued

```
                        1045                1050                1055
Ile Glu Val Asn Ser Ala Val Phe His Pro Asp Asn Val Lys Gly Arg
                1060                1065                1070

Leu Trp Gly Phe Ser Ser Asn Ser Leu Tyr Ser Gln Val Phe Thr Asn
        1075                1080                1085

Thr Gly Leu Thr Glu Thr Gln Asn Ile Ile Gln Ser Lys Ile Lys His
    1090                1095                1100

Met Gln Gln Met Thr Asp Glu Lys Phe Ser Pro Gln Lys Glu Arg Glu
1105                1110                1115                1120

Lys Val Asp Ser Lys Val Gln Glu Ile Thr Asp Lys Gln Ser Lys Met
            1125                1130                1135

Lys Lys Glu Leu Asn Pro Val His Lys Thr Thr Glu Arg Thr Ile Glu
        1140                1145                1150

Gln Glu Gly Pro Ala Pro Glu Ser Pro Ser Thr Gly Met Arg Lys
    1155                1160                1165

<210> SEQ ID NO 9
<211> LENGTH: 36
<212> TYPE: DNA
<213> ORGANISM: Artificial Sequence
<220> FEATURE:
<223> OTHER INFORMATION: Made in a lab

<400> SEQUENCE: 9
aaaaacgcgg atccatggtg ataaacatgg ttgacg                         36

<210> SEQ ID NO 10
<211> LENGTH: 39
<212> TYPE: DNA
<213> ORGANISM: Artificial Sequence
<220> FEATURE:
<223> OTHER INFORMATION: Made in a lab

<400> SEQUENCE: 10
aaaaacgcgt cgacctattt ctttataatt cccgtgtac                      39

<210> SEQ ID NO 11
<211> LENGTH: 37
<212> TYPE: DNA
<213> ORGANISM: Artificial Sequence
<220> FEATURE:
<223> OTHER INFORMATION: Made in a lab

<400> SEQUENCE: 11
aaaaacgcgt cgacttaaat agtaagactc gagttag                        37

<210> SEQ ID NO 12
<211> LENGTH: 38
<212> TYPE: DNA
<213> ORGANISM: Artificial Sequence
<220> FEATURE:
<223> OTHER INFORMATION: Made in a lab

<400> SEQUENCE: 12
aaaaacgcgt cgactcatgc tactattaag catagagg                       38

<210> SEQ ID NO 13
<211> LENGTH: 42
<212> TYPE: DNA
<213> ORGANISM: Artificial Sequence
<220> FEATURE:
<223> OTHER INFORMATION: Made in a lab
```

-continued

```
<400> SEQUENCE: 13
aaaagaatgc ggccgcttac aatttggtaa attcgatttc ac                          42

<210> SEQ ID NO 14
<211> LENGTH: 38
<212> TYPE: DNA
<213> ORGANISM: Artificial Sequence
<220> FEATURE:
<223> OTHER INFORMATION: Made in a lab

<400> SEQUENCE: 14
aaaaacgcgg atccatgcgt tcgattatta cacaaatc                               38

<210> SEQ ID NO 15
<211> LENGTH: 43
<212> TYPE: DNA
<213> ORGANISM: Artificial Sequence
<220> FEATURE:
<223> OTHER INFORMATION: Made in a lab

<400> SEQUENCE: 15
aaaaacgcgt cgactcatga acatggttga caaaataaaa ttc                         43

<210> SEQ ID NO 16
<211> LENGTH: 42
<212> TYPE: DNA
<213> ORGANISM: Artificial Sequence
<220> FEATURE:
<223> OTHER INFORMATION: Made in a lab

<400> SEQUENCE: 16
aaaagaatgc ggccgcctat attgtattcc taacagtttc tc                          42

<210> SEQ ID NO 17
<211> LENGTH: 77
<212> TYPE: DNA
<213> ORGANISM: Artificial Sequence
<220> FEATURE:
<223> OTHER INFORMATION: Made in a lab

<400> SEQUENCE: 17
tatggccatg gatcggagta gggatcgcct acctcctttt gagacagaga cgcgtatcct       60
cggtggtggt ggtggtg                                                     77

<210> SEQ ID NO 18
<211> LENGTH: 79
<212> TYPE: DNA
<213> ORGANISM: Artificial Sequence
<220> FEATURE:
<223> OTHER INFORMATION: Made in a lab

<400> SEQUENCE: 18
gatccaccac caccaccacc gaggatacgc gtctctgtct caaaaggagg taggcgatcc       60
ctactccgat ccatggcca                                                   79
```

BACTERIAL PROTEIN PHOSPHOINOSITIDE PROBES AND EFFECTORS

CROSS-REFERENCE TO RELATED APPLICATIONS

This application claims benefit of U.S. Provisional Application No. 60/719,934 filed on Sep. 23, 2005.

FIELD OF THE INVENTION

The present invention relates to methods for determining the presence or absence of phosphoinositide lipids in a sample. More specifically the method of the present invention allows to determine the presence or absence of phosphatidylinositol(3) phosphate (PI(3)P), phosphatidylinositol(4) phosphate (PI(4)P) or phosphatidyl-inositol(5) phosphate (PI(5)P) in a sample. Additionally, the present invention relates to isolated proteins capable of binding phosphoinositides, protein-phosphatidylinositol constructs, methods for preparing phosphatidylinositol-binding polypeptides and methods for treating disorders.

BACKGROUND OF THE INVENTION

In the environment, the Gram-negative bacterium *Legionella pneumophila* colonizes biofilms and multiplies within various protozoa [1]. Upon transmission to the human lung, the bacteria replicate within alveolar macrophages, and may cause the severe pneumonia Legionnaires' disease [2, 3]. To establish its replicative niche, *L. pneumophila* prevents the fusion of its phagosome with lysosomes [4], and recruits early secretory vesicles at endoplasmic reticulum (ER) exit sites [5]. The resulting *Legionella*-containing vacuole (LCV) is characterized by the ER marker calnexin, the v-SNARE Sec22b, and the small GTPases Arf1 and Rab1 [6, 7]. Moreover, the LCV undergoes a transition from a tight to a spacious vacuole [8, 9] and eventually matures into an acidic vacuole [10], wherein the bacteria multiply independently of the bacterial Icm/Dot type IV secretion system (T4SS) [11]. The Icm/Dot T4SS, a conjugation machinery encoded by 25 different genes, is required for formation of the LCV [12, 13] as well as for modulation of phagocytosis [14, 15].

To date, more than 30 different Icm/Dot-secreted proteins have been identified as putative effectors, many of which form families of 2-6 paralogues [16-22]. The precise function of most of these proteins is not known, owing at least in part to the fact that *L. pneumophila* strains lacking even multiple family members do not show a phenotype with regard to intracellular replication [18, 20, 22]. However, the inability of Icm/dot mutants to direct phagocytosis and establish a LCV, suggests that at least some Icm/Dot-secreted proteins interfere with host cell phagocytosis or vesicle trafficking.

Indeed, the recently identified effectors LepA and LepB share homology with SNAREs and seem to promote the non-lytic release of vesicles containing *L. pneumophila* from amoebae [19]. The first Icm/Dot substrate to be functionally characterized, RalF, recruits the GTPase Arf1 to the LCV and acts as a guanine nucleotide exchange factor for the Arf family of small GTPases [16]. The Icm/Dot-secreted proteins SidC and its paralogue SdcA have no orthologues in the database, their function is unknown, and a sidC/sdcA double mutant shows no phenotype [18]. SdcA was recently identified in a screen using growth inhibition of yeast to select for putative *L. pneumophila* effector proteins [22]. To subvert host cell trafficking, the large number of Icm/Dot-secreted proteins is likely organized in a complex spatial and temporal manner.

In eukaryotic cells, the metabolism of phosphoinositide lipids is pivotal for the regulation of membrane dynamics during phagocytosis, endocytosis and exocytosis [23, 24]. Depending on phosphorylation at position 3, 4 and/or 5 of the D-myo-inositol ring, phosphoinositides recruit specific effectors to distinct membranes in a time- and organelle-dependent manner, thus coordinating intracellular membrane trafficking and actin remodelling, as well as receptor-mediated signal transduction. The central role of phosphoinositide second messengers is exploited by a number of intracellular bacterial pathogens [25], for example *Shigella flexneri* [26] and *Salmonella enterica* [27, 28] employ type III-secreted phosphoinositide phosphatases to modulate phosphoinositide metabolism during bacterial entry and intracellular replication.

Phosphoinositide metabolism is well characterized in the social amoeba *Dictyostelium discoideum* [29, 30], which supports Icm/Dot-dependent intracellular replication of *L. pneumophila* [31-33]. Here, we use a *Dictyostelium* strain lacking the class I PI(3) kinase (PI3K)-1 and -2 (ΔPI3K1/2; [34]) to demonstrate a role for phosphoinositide metabolism in phagocytosis, trafficking and intracellular replication of *L. pneumophila*. Furthermore, we identify Icm/Dot-secreted proteins, which specifically bind to PI(4)P, thus providing a mechanistic link between phosphoinositide metabolism and the subversion of host cell trafficking by *L. pneumophila*.

SUMMARY OF THE INVENTION

The inventors have unexpectedly found that bacterial proteins, or functional equivalents thereof, directly and specifically bind to certain phosphoinositide lipids in vitro and on the *Legionella*-containing vacuole (LCV) in infected host cells, thus linking Icm/Dot-dependent secretion and bacterial replication to host cell phosphoinositide metabolism. The present invention provides a method for detecting and quantifying phosphoinositide lipids in a sample.

It was found, for example, that *L. pneumophila* SidC and SdcA directly and specifically bind to PI(4)P in vitro and on LCVs in infected host cells. It was also found that *L. pneumophila* LepB, LidA and Lpg2311 directly bind to monophosphorylated phosphoinositides in vitro.

Moreover, the inventors have also surprisingly found that, in the context of liposomes, SidC also strongly binds PI(4)P, but not PI(3)P or PI(4,5)P2. SidC and SdcA are not predicted to contain a PH domain or other phosphoinositide-binding domains, and therefore, harbor a novel PI(4)P-binding domain or novel PI(4)P-binding domains.

In one aspect, the present invention comprises novel SidC- and SdcA-derived fragments, or fusion proteins based upon those fragments, as PI(4)P probes in biochemical and cell biological assays. Applications of the probes include: (i) detection and quantification of PI(4)P in vitro, (ii) staining of intracellular compartments in live or fixed eukaryotic cells, (iii) use in lipid-protein overlay experiments, (iv) enrichment of PI(4)P-containing cellular compartments by pull down assays, and (v) ectopical expression, e.g. as a GFP fusion protein.

According to a further aspect of the present invention, full length SidC, SdcA and further *Legionella*-derived proteins, and fragments thereof, are stable and robustly bind PI(4)P even after cycles of shock freezing and thawing.

The inventors have found that SidC specifically binds to PI(4)P but not to other phosphoinositides or other lipids. It was established that GST-SidC can be readily overexpressed in *E. coli* (e.g. strain BL21(DE3)) in a predominantly soluble form and purified by glutathione affinity chromatography. The yield is up to 25 mg/l LB medium. GST-SidC is stable and withstands repeated cycles of freezing/thawing without loss of PI(4)P-binding activity. Thus, SidC is a robust probe. Moreover, the PI(4)P-binding domain is significantly smaller than, for example, a PI(4)P-binding antibody.

The present invention is also directed towards pharmaceutical compositions and methods of preparing PI(4)P-binding polypeptides.

In a further aspect, a method of treating a disorder or disease in which abnormal levels of PI(4)P are implicated in a patient is provided. The treatment comprises administering to the patient a PI(4)P-binding polypeptide or a fusion protein comprising such a polypeptide.

Furthermore, the present invention provides a rationale for the observed toxicity of SdcA expressed in yeast. SidC and SdcA have a deleterious effect on essential PI(4)P- and/or PI(3)P-mediated vesicle trafficking, either by titrating PI(4)P membrane anchors for host cell effectors or by functioning as effectors that interfere with vesicle trafficking directly. Given that SidC and SdcA modulate vesicle trafficking, the proteins or fragments thereof can be used as therapeutic agents in human diseases caused by defects in phosphoinositide signaling, including, but not limited to, Lowe syndrome [55].

The Icm/Dot T4SS is well established as a pivotal virulence determinant of *L. pneumophila*, which governs phagocytosis as well as intracellular trafficking of the bacteria. Contrarily, the activities and host cell targets of most of the Icm/Dot-secreted effector proteins remain obscure. Here, we analyzed the role of host cell PI3Ks during phagocytosis and intracellular replication of *L. pneumophila* and identify Icm/Dot-secreted proteins which directly engage PI(4)P.

Wild-type *L. pneumophila* upregulates phagocytosis by *Dictyostelium* (FIG. 1, 2), as shown previously using macrophages or *Acanthamoeba castellanii* as host cells [14]. PI3Ks were found to be dispensable for uptake of wild-type *L. pneumophila* by *Dictyostelium* but involved in phagocytosis and degradation of an *L. pneumophila* ΔicmT mutant. Therefore, *L. pneumophila* apparently employs a specific phagocytic pathway, which bypasses a requirement for PI3Ks. This pathway is distinct from PI3K-dependent phagocytosis of non-invasive or other pathogenic bacteria, including *Listeria monocytogenes* or uropathogenic *E. coli* [25].

Figure 2:
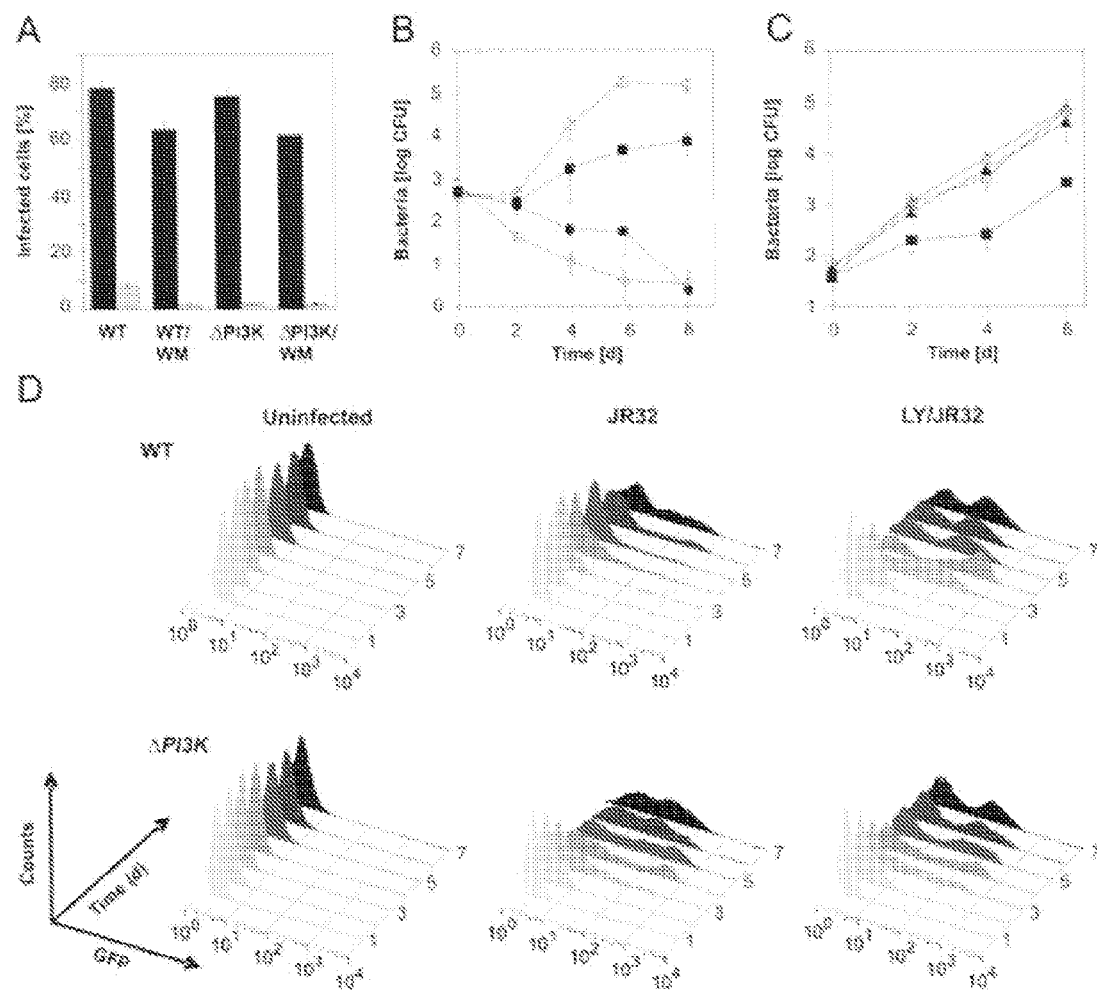

We provided genetic and pharmacological evidence that class I PI3Ks are involved in intracellular replication and trafficking of wild-type *L. pneumophila* (FIG. 2, 4). In the absence of PI3Ks, *L. pneumophila* replicated more efficiently and, at the same time, the transition from tight to spacious vacuoles was inhibited. In contrast, in a *Dictyostelium* rtoA mutant, the defective transition of LCVs from tight to spacious vacuoles coincided with a decreased efficiency of intracellular replication of *L. pneumophila* [8]. Our results suggest that the "maturation" of tight to spacious vacuoles is not required for formation of a replication-permissive vacuole. PI3Ks have been implicated in homotypic phagosome fusion and formation of spacious phagosomes [38]. Accordingly, PI3K-dependent formation of spacious phagosomes may represent a host cell process which does not support (or even counteracts) the formation of a replication-permissive LCV.

Formation of the LCV takes place at ER exit sites and requires a functional early secretory pathway [5-7]. Since class I PI3Ks play a role in degradation of ΔicmT (FIG. 3) and the modulation of the LCV (FIG. 4A, B), absence of PI3Ks might contribute to a more efficient intracellular replication of *L. pneumophila* in two synergistic ways: (i) by rendering the degradative endocytic pathway less efficient and (ii) by promoting interactions of the LCV with the secretory pathway. The PI3K products $PI(3,4,5)P_3$ and $PI(3)P$ have been shown to promote phagocytosis, endocytosis, and bacterial degradation [23]. Absence of these phosphoinositides might therefore account for the observed defects in degradation of ΔicmT and render evasion of the degradative pathway by wild-type *L. pneumophila* more efficient. On the other hand, the effect of PI3Ks on trafficking of LCVs along the secretory pathway perhaps involves PI(4)P, which in absence of PI3Ks is more abundant in *Dictyostelium* [36] and thus might accumulate locally on LCVs. The discovery that the Icm/Dot-secreted proteins SidC and SdcA bind PI(4)P in vitro (FIG. 5) and anchor to the LCV in infected *Dictyostelium* preferentially in the absence of PI3Ks (FIG. 6) supports this hypothesis. To account for their effect on the secretory pathway, PI3Ks may be recruited. More likely, however, the absence of PI3Ks affects the modulation of LCVs in trans by increasing the cellular concentration of PI(4)P.

Figure 4:
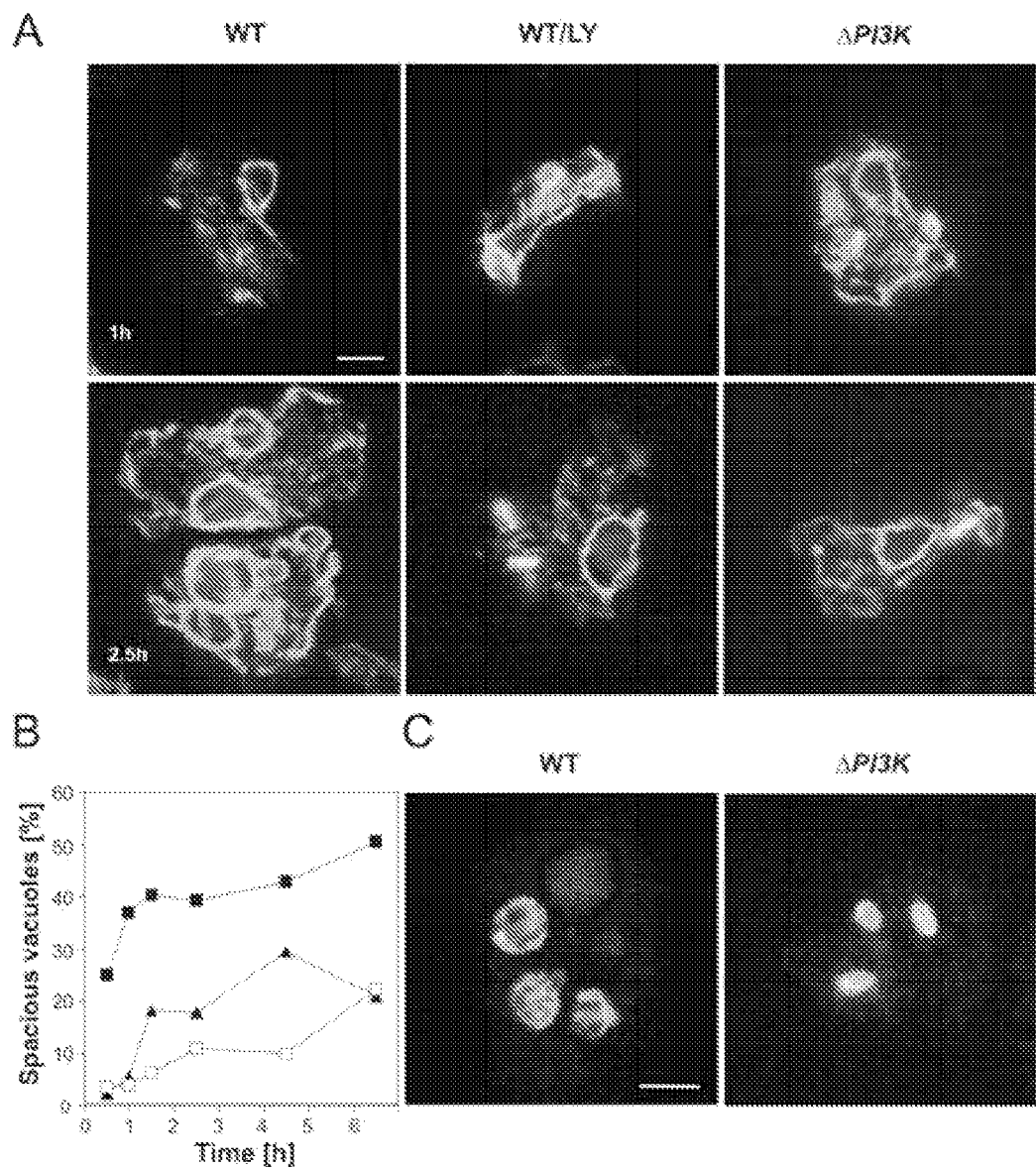

The identification of Icm/Dot-secreted *L. pneumophila* proteins specifically binding to PI(4)P identifies this phosphoinositide as a lipid marker of the LCV. PI(4)P selectively accumulates in the trans Golgi complex and regulates exocytosis by a poorly defined mechanism [24]. PI(4)P is the first lipid marker and the first Golgi marker identified on the LCV. SidC secreted by *L. pneumophila* selectively bound to the LCV, but not to other cellular vesicles, even if overexpressed as an M45-tagged protein (FIG. 4C, 6). To account for this specificity, SidC perhaps engages a co-receptor on the LCV, which increases the affinity to PI(4)P of the purified protein alone observed in vitro (FIG. 5).

By anchoring to PI(4)P, SidC and SdcA either (i) directly engage in vesicle trafficking and formation of a replicative vacuole via (an) effector domains, or (ii) serve as adaptors for other *L. pneumophila* effectors involved in formation of the replicative vacuole or exit of the bacteria from host cells. SidC and its upstream paralogue SdcA have no orthologues in the database yet are found in the genomes of all three *L. pneumophila* strains (Philadelphia, Paris, Lens) sequenced to date [39, 40]. The proteins are not predicted to contain a PH or other phosphoinositide-binding domains and, therefore, likely harbor a novel PI(4)P-binding domain which, due to its exquisite specificity, may effectively be employed as a selective PI(4)P probe.

In one aspect, the present invention provides methods for determining the presence or absence of a phosphoinositide lipid in a sample, such as a biological sample. Such methods comprise contacting the sample with a polypeptide and determining whether the compound binds to the phosphoinositide lipid, wherein the polypeptide comprises a sequence selected from the group consisting of: a) sequences having at least 60% identity to a sequence of SEQ ID NO: 1 or 2; b) sequences having at least 80% identity to a sequence of SEQ ID NO: 1 or 2; c) sequences having at least 90% identity to a sequence of SEQ ID NO: 1 or 2; d) sequences having at least 95% identity to a sequence of SEQ ID NO: 1 or 2; d) naturally occurring allelic variants of SEQ ID NO: 1 or 2; e) a fragment of SEQ ID NO: 1 or 2; f) SEQ ID NO: 1 or 2; g) *Legionella pneumophila* SidC; h) *Legionella pneumophila* SdcA; i) *Legionella pneumophila* LidA; j) *Legionella pneumophila* LepA; k) *Legionella pneumophila* LepB; l) *Legionella pneumophila* Lpg2311; and m) C-terminal fragments of SidC: SidC_3C (36 kDa), SidC_3-4 (20 kDa). Diagnostic kits comprising such polypeptides are also provided.

In one embodiment, the phosphoinositide lipid is phosphatidylinositol(4) phosphate and the polypeptide comprises a sequence selected from the group consisting of: a) sequences having at least 60% identity to a sequence of SEQ ID NO: 1 or 2; b) sequences having at least 80% identity to a sequence of SEQ ID NO: 1 or 2; c) sequences having at least 90% identity to a sequence of SEQ ID NO: 1 or 2; d)

sequences having at least 95% identity to a sequence of SEQ ID NO: 1 or 2; d) naturally occurring allelic variants of SEQ ID NO: 1 or 2; e) a fragment of SEQ ID NO: 1 or 2; f) SEQ ID NO: 1 or 2; g) *Legionella pneumophila* SidC; h) *Legionella pneumophila* SdcA; i) *Legionella pneumophila* LidA; j) *Legionella pneumophila* LepB; k) *Legionella pneumophila* Lpg2311; and 1) C-terminal fragments of SidC: SidC__3C (36 kDa), SidC__3-4 (20 kDa).

In a further embodiment, the phosphoinositide lipid is phosphatidylinositol(3) phosphate and the polypeptide comprises a sequence selected from the group consisting of: a) *Legionella pneumophila* LepA; b) *Legionella pneumophila* LepB; c) *Legionella pneumophila* Lpg2311; and d) *Legionella pneumophila* LidA. In yet another embodiment, the phosphoinositide lipid is phosphatidylinositol(5) phosphate and the polypeptide comprises a sequence selected from the group consisting of: a) *Legionella pneumophila* Lpg2311; and b) *Legionella pneumophila* LidA.

The polypeptides employed in such methods may be fused with or conjugated to a tag. For example, the tags and detection methods may include: i) GST, M45, Myc, HA, His and antibody (against tag), ii) fluorescent proteins and fluorescence, iii) fluorophores and fluorescence, iv) biotin and avidin-peroxidase or avidin-fluorophor, and v) colloidal gold and electron microscopy.

In another aspect, the present invention provides isolated polypeptides comprising an amino acid sequence of SEQ ID NO: 1 or 2, together with variants and functional portions, or fragments, thereof. In certain embodiments, such variants are capable of binding a phosphoinositide, such as phosphatidylinositol(4) phosphate.

Fusion proteins comprising such polypeptide are also provided. In certain embodiments, the polypeptide is operatively fused or conjugated to a tag selected from the group consisting of: i) GST, M45, Myc, HA, His, ii) fluorescent proteins, iii) fluorophores, iv) biotin, and v) colloidal gold.

In a further aspect, polypeptide-phosphatidylinositol constructs comprising a polypeptide bound to phosphatidylinositol(4) phosphate (PI(4)P) are provided, wherein the polypeptide comprises a sequence selected from the group consisting of: a) sequences having at least 60%, 80%, 90% or 95% identity to SEQ ID NO: 1 or 2; b) naturally occurring allelic variants of SEQ ID NO: 1 or 2; c) functional portions or fragments of SEQ ID NO: 1 or 2; d) SEQ ID NO: 1 or 2; e) *Legionella pneumophila* SidC; f) *Legionella pneumophila* SdcA; g) *Legionella pneumophila* LidA; h) *Legionella pneumophila* LepB; and k) *Legionella pneumophila* Lpg2311.

Pharmaceutical compositions comprising the polypeptides and/or fusion proteins disclosed herein together with a pharmaceutically acceptable carrier are also provided, together with methods of treating a disorder characterized by the presence of abnormal levels of PI(4)P by administering to a patient a therapeutically effective amount of the pharmaceutical composition.

In yet a further aspect, the present invention provides methods for preparing a PI(4)P binding polypeptide, a functional equivalent thereof or a fusion protein comprising such a polypeptide. In certain embodiments such methods comprise: (a) introducing a vector comprising a nucleic acid molecule coding for the polypeptide, functional equivalent or fusion protein into a host cell; (b) culturing the host cell under conditions wherein the PI(4)P binding polypeptide, functional equivalent or fusion protein is expressed; and (c) recovering the PI(4)P binding polypeptide, functional equivalent or fusion protein.

BRIEF DESCRIPTION OF THE FIGURES

The invention described herein will be more fully understood from the detailed description given below and the accompanying figures, which should not be considered limiting to the invention described in the appended claims.

FIG. 1 Phagocytosis of wild-type *L. pneumophila* or ΔicmT by *Dictyostelium*. Phagocytosis of gfp-expressing wild-type *L. pneumophila* or ΔicmT by *Dictyostelium* infected at (A, B) an MOI of 100, or (C) at the MOI indicated was analyzed by flow cytometry. The increase in GFP fluorescence (FL 1, x-axis) indicates that, at MOIs ranging from 1-100, the number of wild-type *L. pneumophila* phagocytosed is about one order of magnitude higher than the number of ΔicmT. Phagocytosis is blocked by latrunculin B or incubation at 4° C. The data shown (B, C) are the means and standard deviations of duplicates and representative of at least three independent experiments.

FIG. 2 A role for PI3Ks in intracellular replication but not phagocytosis of wild-type *L. pneumophila*. (A) Phagocytosis by *Dictyostelium* wild-type Ax3 or ΔPI3K1/2 (untreated or treated with 5 μM wortmannin (WM)) of GFP-labeled *L. pneumophila* wild-type (black bars) or a ΔicmT mutant strain (grey bars) was determined by flow cytometry. (B) Release of *L. pneumophila* wild-type (squares) or ΔicmT (circles) into the supernatant of *Dictyostelium* wild-type (closed symbols) or ΔPI3K1/2 (open symbols) was quantified by CFUs. (C) Release of wild-type *L. pneumophila* (CFUs) from *Dictyostelium* wild-type (untreated, ■; 10 μM LY294002 (LY), ▲) or ΔPI3K1/2 (untreated, □; LY, Δ). (D) Quantification by flow cytometry of intracellular growth of GFP-labeled wild-type *L. pneumophila* within wild-type *Dictyostelium* or ΔPI3K1/2 in presence or absence of 20 μM LY. The data shown are means and standard deviations of duplicates (A) or triplicates (B, C) and representative of at least three independent experiments (A-D).

FIG. 3 A role for PI3Ks in degradation of *L. pneumophila* ΔicmT. Quantification by flow cytometry of intracellular degradation of GFP-labeled *L. pneumophila* ΔicmT (MOI 100, MOI 500) within wild-type *Dictyostelium* or ΔPI3K1/2 in presence or absence of 20 μM LY. In the absence of PI3Ks, ΔicmT is less efficiently phagocytosed and degraded.

FIG. 4 Trafficking of *L. pneumophila* within *Dictyostelium* lacking functional PI3Ks. (A) Confocal laser scanning micrographs of calnexin-GFP-labeled (green) *Dictyostelium* wild-type Ax3 (untreated or treated with 20 μM LY) or ΔPI3K1/2 infected with DsRed-labeled wild-type *L. pneumophila* (red) for 1 h or 2.5 h, respectively. DNA was stained with DAPI (blue). (B) Quantification over time of spacious *Legionella*-containing vacuoles (LCV) in calnexin-GFP-labeled *Dictyostelium* wild-type (untreated, ■; or treated with LY, ▲) or ΔPI3K1/2 (□) infected with DsRed-labeled wild-type *L. pneumophila*. Data represent percentage of spacious vacuoles from 50-200 total vacuoles per time point scored in 4 independent experiments. (C) Confocal laser scanning micrographs of *Dictyostelium* wild-type or ΔPI3K1/2, infected for 75 min with wild-type *L. pneumophila* expressing M45-tagged SidC. Infected amoebae were stained with rhodamine-conjugated anti *L. pneumophila* antibody (red), FITC-conjugated anti M45-tag antibody (green), and DAPI (blue), respectively. Bars, 2 μm.

FIG. 5A Binding of *L. pneumophila* Icm/Dot-secreted proteins to phosphoinositides in vitro. Binding of affinity-purified GST fusion proteins of SidC, SdcA, SidD or SdhB (160 pmol) to different lipids (100 pmol; left panels) or twofold serial dilutions of phosphoinositides (100-1.56 pmol; right panels) immobilized on nitrocellulose membranes was analyzed by a protein-lipid overlay assay using an anti GST antibody and enhanced chemiluminescence. Phosphoinositides (PI), lysophosphatidic acid (LPA); lysophosphocholine (LPC), phosphatidylethanolamine (PE), phosphatidylcholine (PC), sphingosine-1-phosphate (SP), phosphatidic acid (PA), phosphatidylserine (PS). The experiment was reproduced at least three times with similar results.

Figure 5A:
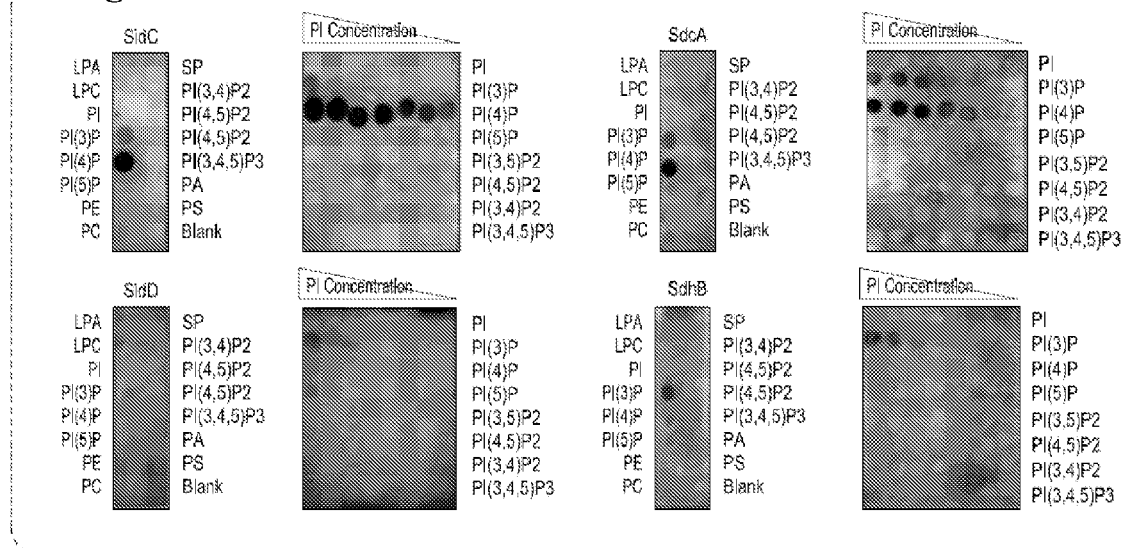
Figure 5B:
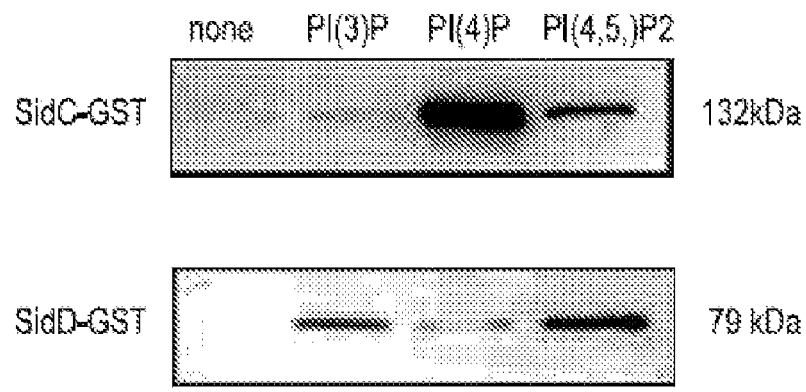

FIG. 5B Binding of *L. pneumophila* Icm/Dot-secreted proteins to phosphoinositides in vitro. Phospholipid (PL) vesicles (20 µl, 1 mM lipid) composed of PC (65%), PE (30%), and 5% (1 nmol) either PI(4)P, PI(3)P or PI(4,5)$P_2$ were incubated with affinity-purified GST-SidC or GST-SidD (40 pmol), centrifuged and washed. Binding of GST fusion proteins to PL vesicles was assayed by Western blot with an anti GST antibody. Similar results were obtained in three separate experiments.

Figure 5C:
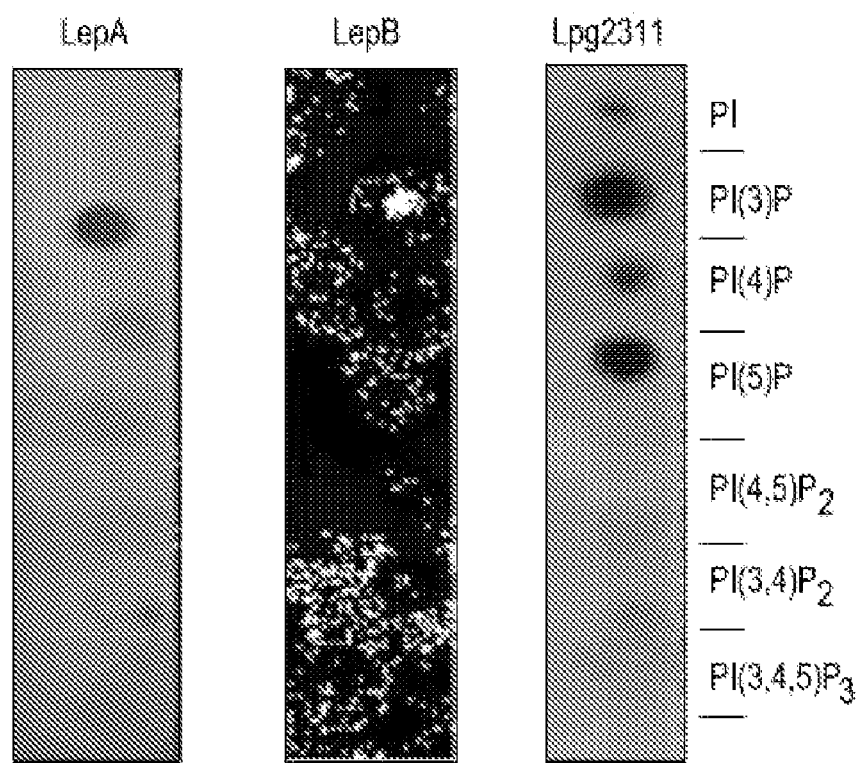

FIG. 5C Binding of *L. pneumophila* proteins LepA, LepB and Lpg2311 to phosphoinositides in vitro. Binding of GST fusion proteins to different synthetic di-hexadecanoyl-phosphoinositides (100 pmol) immobilized on nitrocellulose membranes was analyzed by a protein-lipid overlay assay using an anti GST antibody. The fusion proteins specifically bind mono-phosphorylated phosphoinositides.

Figure 5D:
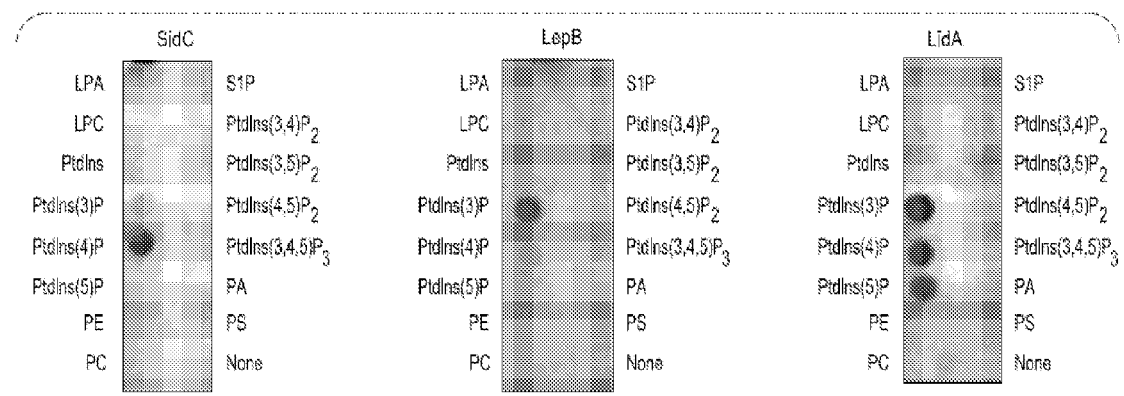

FIG. 5D Binding of the *L. pneumophila* proteins SidC, LepB and LidA to phosphoinositides in vitro. Binding of GST effector fusion proteins to different synthetic di-hexadecanoyl-phosphoinositides (100 pmol) immobilized on nitrocellulose membranes was analyzed by a protein-lipid overlay assay using an anti GST antibody. While SidC specifically binds to PI(4)P, LepB binds PI(3)P and LidA binds monophosphorylated phosphoinositides. Abbreviation: phosphatidylinositol (PtdIns).

Figure 5E:
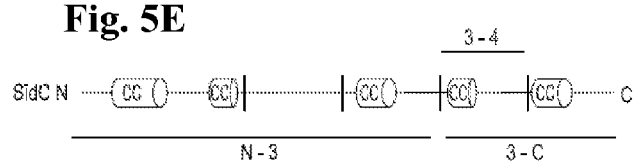

FIG. 5E Domain analysis of SidC (CC: coiled coils) and fragments tested (vertical lines).

Figure 5F:
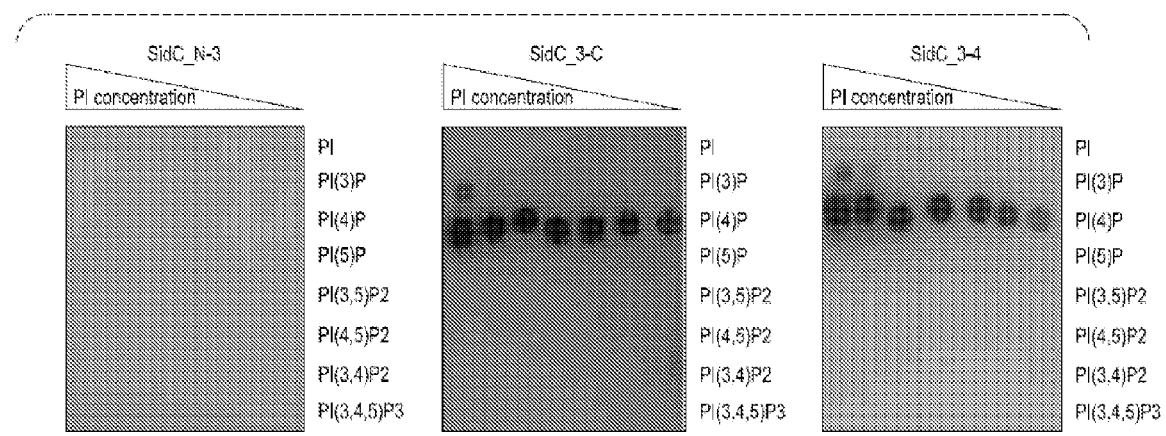

FIG. 5F Binding of affinity-purified GST fusion proteins of SidC fragments to different phosphoinositides spotted in 2-fold serial dilutions (100-1.56 pmol) onto nitrocellulose membranes. Binding was determined by a protein-lipid overlay assay using an anti-GST antibody.

FIG. 6 PI3Ks affect the amount of SidC bound to *Legionella*-containing vacuoles in *Dictyostelium*. (A) Confocal laser scanning micrographs of calnexin-GFP-labeled *Dictyostelium* wild-type strain Ax3 (green), infected with DsRed-labeled wild-type *L. pneumophila* (red) for 1 h (left panel), and immuno-labeled for SidC (blue) with an affinity purified primary and Cy5-conjugated secondary antibody (middle panel). To quantify fluorescence intensity (right panel), the averaged fluorescence intensity within background areas ("B1-3") was subtracted from the intensity of the sample area ("S"). Bar, 2 µm. (B) Dot plot of SidC fluorescence (average and variance) on LCVs within *Dictyostelium* wild-type (untreated, n=135; treated with 20 PM LY, n=94) or ΔPI3K1/2 (n=86). The data shown are combined from 6 independent experiments, each normalized to 100% (average SidC fluorescence on LCVs in wild-type *Dictyostelium*).

FIG. 7 PI(4)P is a lipid marker of LCVs harboring Icm/Dot-proficient *L. pneumophila* (A, B, and D). Confocal micrographs of LCVs in lysates of (A) calnexin-GFP-labeled *Dictyostelium*, (B) VatM-GFP-labeled *Dictyostelium*, or (D) RAW264.7 macrophages infected with DsRed-Express-labeled *L. pneumophila* are shown. The lysates were prepared with a ball homogenizer, and PI(4)P was visualized on the LCVs using as probes either the PH domain of the PI(4)P-binding protein FAPP1 fused to GST, an antibody against PI(4)P, or GST-SidC. Using GST alone or omission of the anti-PI(4)P antibody did not label the LCVs. Bar denotes 2 µm (magnification of all images is identical). (C) Quantification of PI(4)P-positive calnexin-GFP-labeled (n=300) or VatM-GFP-labeled (n=100) LCVs in *Dictyostelium* wild-type strain Ax3.

Figure 8A:
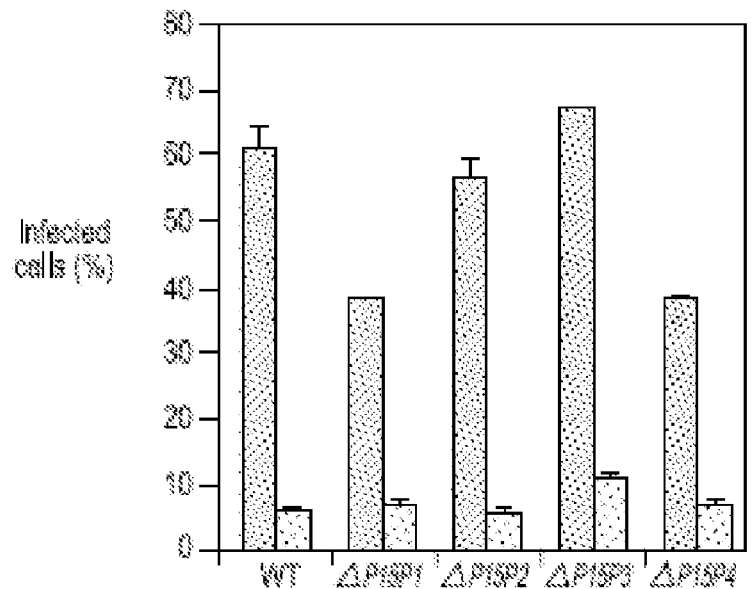
Figure 8B:
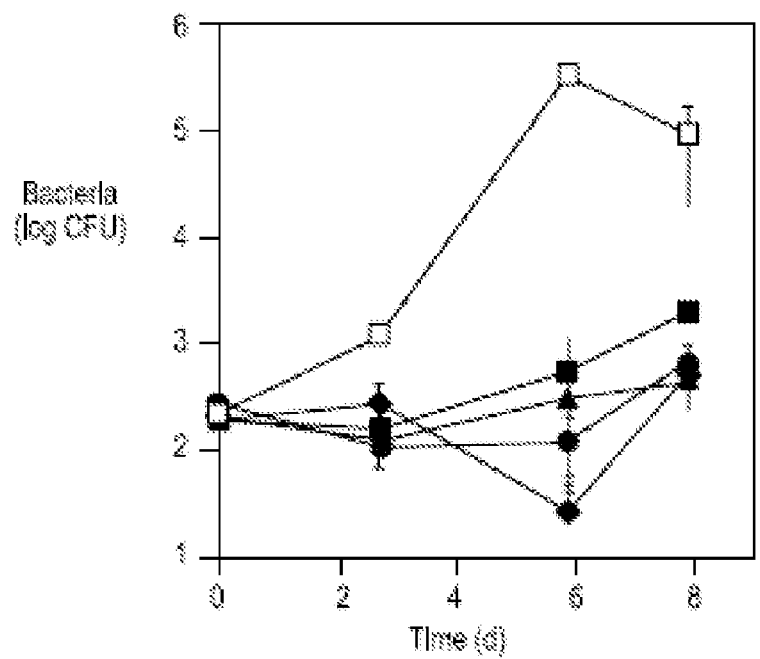

FIG. 8 Uptake and intracellular replication of *L. pneumophila* in *Dictyostelium* PI(5)P phosphatase mutants. Uptake of *L. pneumophila* was analyzed by FACS using GFP-expressing bacteria. (A) Deletion of *Dictyostelium* PI(5)P phosphatases barely affected uptake of *L. pneumophila* wild-type (black bars) or ΔicmT (grey bars). (B) *L. pneumophila* grew more efficiently in *Dictyostelium* lacking PI(5)P phosphatase-4 (open squares) but not other PI(5)P phosphatases.

FIG. 9 Polynucleotide sequence for *Legionella pneumophila* SidC (SEQ ID NO: 3).

FIG. 10 Polynucleotide sequence for *Legionella pneumophila* SdcA (SEQ ID NO: 4).

FIG. 11 Amino acid sequence for *Legionella pneumophila* LepA (SEQ ID NO: 5).

FIG. 12 Amino acid sequence for *Legionella pneumophila* LepB (SEQ ID NO: 6).

FIG. 13 Amino acid sequence for *Legionella pneumophila* LidA (SEQ ID NO: 7).

FIG. 14. Amino acid sequence for *Legionella pneumophila* Lpg2311 (SEQ ID NO: 8).

DETAILED DESCRIPTION

In certain embodiments, the present invention provides isolated polypeptides comprising a sequence selected from the group consisting of SEQ ID NO: 1 and 2 and variants thereof. As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 60%, more preferably at least 75%, more preferably at least 80%, more preferably at least 85%, more preferably yet at least 90%, and most preferably at least 95% or 98% identity to a specific sequence disclosed herein. The percentage identity is determined by aligning the two sequences to be compared as described below, determining the number of identical residues in the aligned portion, dividing that number by the total number of residues in the inventive (queried) sequence, and multiplying the result by 100.

Polynucleotide and polypeptide sequences having a specified percentage identity to a polynucleotide or polypeptide disclosed herein share a high degree of similarity in their primary structure. In addition to a specified percentage identity to a polynucleotide or polypeptide of the present invention, variant polynucleotides and polypeptides preferably have additional structural and/or functional features in common with a polynucleotide or polypeptide of the present invention. Polynucleotides having a specified degree of identity to, or capable of hybridizing to, a polynucleotide disclosed herein preferably additionally have at least one of the following features: (1) they contain an open reading frame, or partial open reading frame, encoding a polypeptide, or a functional portion of a polypeptide, having substantially the same functional properties as the polypeptide, or functional portion thereof, encoded by a polynucleotide in a recited SEQ ID NO; or (2) they contain identifiable domains in common.

Polynucleotide or polypeptide sequences may be aligned, and percentages of identical nucleotides or amino acids in a specified region may be determined against another polynucleotide or polypeptide, using computer algorithms that are publicly available. The BLASTN and FASTA algorithms, set to the default parameters described in the documentation and distributed with the algorithm, may be used for aligning and identifying the similarity of polynucleotide sequences. The alignment and similarity of polypeptide sequences may be examined using the BLASTP algorithm. BLASTX and FASTX algorithms compare nucleotide query sequences translated in all reading frames against polypeptide sequences. The FASTA and FASTX algorithms are described in Pearson and Lipman, *Proc. Natl. Acad. Sci. USA* 85:2444-2448, 1988; and in Pearson, *Methods in Enzymol.* 183:63-98, 1990. The FASTA software package is available from the University of Virginia by contacting the Assistant Provost for Research, University of Virginia, PO Box 9025, Charlottesville, Va. 22906-9025. The BLASTN software is available from the National Centre for Biotechnology Information (NCBI), National Library of Medicine, Building 38A, Room 8N805, Bethesda, Md. 20894. The BLASTN algorithm Version 2.0.11 [Jan-20-2000] set to the default parameters described in the documentation and distributed with the algorithm, is preferred for use in the determination of polynucleotide variants according to the present invention. The use of the BLAST family of algorithms, including BLASTN, BLASTP and BLASTX, is described in the publication of Altschul et al., "Gapped BLAST and PSI-BLAST: a new generation of protein database search programs," *Nucleic Acids Res.* 25:3389-3402, 1997.

The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

As noted above, the percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity. By way of example, a queried polynucleotide having 220 nucleic acids has a hit to a polynucleotide sequence in the EMBL database having 520 nucleic acids over a stretch of 23 nucleotides in the alignment produced by the BLASTN algorithm using the default parameters. The 23-nucleotide hit includes 21 identical nucleotides, one gap and one different nucleotide. The percentage identity of the queried polynucleotide to the hit in the EMBL database is thus 21/220 times 100, or 9.5%. The percentage identity of polypeptide sequences may be determined in a similar fashion.

Polypeptides comprising sequences that differ from the specific polypeptide sequences disclosed herein as a result of amino acid substitutions, insertions, and/or deletions totaling less than 10% of the total sequence length are contemplated by and encompassed within the present invention, provided the variant polypeptide has functional properties which are substantially the same as, or substantially similar to, those of the specific polypeptide disclosed herein.

All of the polynucleotides and polypeptides described herein are isolated and purified, as those terms are commonly used in the art. Preferably, the polypeptides and polynucleotides are at least about 80% pure, more preferably at least about 90% pure, and most preferably at least about 99% pure.

As used herein, the term "polypeptide" encompasses amino acid chains of any length, including full-length proteins, wherein the amino acid residues are linked by covalent peptide bonds. The term "polypeptide encoded by a polynucleotide" as used herein, includes polypeptides encoded by a polynucleotide that comprises a partial isolated polynucleotide sequence provided herein. Polypeptides of the present invention may be naturally purified products, or may be produced partially or wholly using recombinant techniques.

Polypeptides of the present invention may be produced recombinantly by inserting a polynucleotide sequence of the present invention encoding the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a polynucleotide molecule that encodes a recombinant polypeptide. Suitable host cells include prokaryotes, yeast, and higher eukaryotic cells. Preferably, the host cells employed are plant, *E. coli*, insect, yeast, or a mammalian cell line such as COS or CHO.

In a related aspect, polypeptides are disclosed that comprise at least a functional portion, or fragment, of a polypeptide having a specific SEQ ID NO: disclosed herein. As used herein, the "functional portion" of a polypeptide is that portion which contains the active site essential for affecting the function of the polypeptide, for example, the portion of the molecule that is capable of binding a phosphoinositide lipid. Such functional portions generally comprise at least about 5 amino acid residues, more preferably at least about 10, and most preferably at least about 20 amino acid residues. Functional portions of a polypeptide may be identified by first preparing fragments of the polypeptide, by either chemical or enzymatic digestion of the polypeptide or mutation analysis of the polynucleotide that encodes for the polypeptide, and subsequently expressing the resultant mutant polypeptides. The polypeptide fragments or mutant polypeptides are then tested to determine which portions retain the biological activity of the full-length polypeptide.

Portions and other variants of polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (Merrifield, *J. Am. Chem. Soc.* 85:2149-2154, 1963). Equipment for automated synthesis of polypeptides is available from suppliers such as Perkin Elmer/Applied BioSystems, Inc. (Foster City, Calif.), and may be operated according to the manufacturer's instructions. Variants of a native polypeptide may be prepared using standard mutagenesis techniques, such as oligonucleotide-directed site-specific mutagenesis (see, for example, Kunkel, *Proc. Natl. Acad. Sci. USA* 82:488-492, 1985). Sections of DNA sequence may also be removed using standard techniques to permit preparation of truncated polypeptides.

Fusion proteins comprising a first polypeptide disclosed herein and a second, known, polypeptide, together with variants of such fusion proteins, are also provided. Fusion proteins may include a linker peptide between the first and second polypeptides.

A polynucleotide encoding a fusion protein is constructed using known recombinant DNA techniques to assemble separate polynucleotides encoding the first and second polypeptides into an appropriate expression vector. The 3' end of a polynucleotide encoding the first polypeptide is ligated, with or without a peptide linker, to the 5' end of a DNA sequence polynucleotide encoding the second polypeptide so that the reading frames of the sequences are in phase to permit mRNA translation of the two polynucleotides into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. The linker sequence may be from 1 to about 50 amino acids in length. Peptide linker sequences are not required when the first and second polypeptides have non-essential N-terminal amino acid regions that can be used to separate the functional domains and prevent steric interference. The ligated polynucleotides encoding the fusion proteins are cloned into suitable expression systems using techniques known to those of ordinary skill in the art.

Methods are provided for using one or more of the disclosed polypeptides, functional portions thereof and fusion proteins to treat a disorder in a patient, such as a disorder characterized by an unwanted and/or deleterious level of phosphatidylinositol(4) phosphate. As used herein, a "patient" refers to any warm-blooded animal, preferably a human.

In this aspect, the polypeptide, functional portion thereof or fusion protein (referred to as the "active component") is generally present within a composition, such as a pharmaceutical or immunogenic composition. Such compositions may comprise one or more active components and a physiologically acceptable carrier. Immunogenic compositions may comprise one or more of the active components and an immunostimulant, such as an adjuvant or a liposome.

Routes and frequency of administration, as well as dosage, vary from individual to individual. In general, the compositions may be administered by injection (e.g., intradermal, intramuscular, intravenous or subcutaneous), intranasally (e.g., by aspiration) or orally. In general, the amount of binding agent present in a dose ranges from about 1 pg to about 100 mg per kg of host, typically from about 10 pg to about 1 mg per kg of host, and preferably from about 100 pg to about 1 µg per kg of host. Suitable dose sizes will vary with the size of the patient, but will typically range from about 0.1 ml to about 2 ml.

While any suitable carrier known to those of ordinary skill in the art may be employed in the compositions, the type of carrier will vary depending on the mode of administration. For parenteral administration, such as subcutaneous injection, the carrier preferably comprises water, saline, alcohol, a lipid, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the compositions to non-specifically enhance the immune response. Most adjuvants contain a substance designed to protect against rapid catabolism, such as aluminum hydroxide or mineral oil, and a non-specific stimulator of immune responses, such as lipid A, *Bordetella pertussis* or M. tuberculosis. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

As noted above, the disclosed polypeptides, functional portions thereof and fusion proteins disclosed herein may be used to determine the presence or absence of a phosphoinositide lipid in a biological sample. Examples of biological samples that may be used in such methods include, but are not limited to, blood, sera, saliva, urine, cerebrospinal fluid, synovial fluid, mucus, and/or tissue biopsies.

There are a variety of assay formats known to those of ordinary skill in the art for use in such methods. See, e.g., Harlow and Lane, *Antibodies: A Laboratory Manual*, Cold Spring Harbor Laboratory, 1988. In general, the presence or absence of a phosphoinositide lipid may be determined by (a) contacting a biological sample obtained from a patient with a polypeptide disclosed herein; (b) detecting in the sample a level of phosphoinositide lipid that binds to the polypeptide; and (c) comparing the level of phosphoinositide lipid with a predetermined cut-off value.

In one embodiment, the assay involves the use of polypeptide immobilized on a solid support to bind to and remove the phosphoinositide lipid from the sample. The bound phosphoinositide lipid may then be detected using a detection reagent that contains a reporter group and specifically binds to the phosphoinositide lipid/polypeptide complex. Such detection reagents may comprise, for example, a binding agent that specifically binds to the polypeptide.

The solid support may be any material known to those of ordinary skill in the art to which the polypeptide may be attached. For example, the solid support may be a test well in a microtiter plate or a nitrocellulose membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The polypeptide may be immobilized on the solid support using a variety of techniques known to those of skill in the art, which are amply described in the patent and scientific literature. As used herein, the term "immobilization" refers to both noncovalent association, such as adsorption, and covalent attachment (which may be a direct linkage between the agent and functional groups on the support or may be a linkage by way of a cross-linking agent).

Immobilization by adsorption to a well in a microtiter plate or to a membrane may be preferred. In such cases, adsorption may be achieved by contacting the polypeptide, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of polypeptide ranging from about 10 ng to about 10 µg, and preferably about 100 ng to about 1 µg, is sufficient to immobilize an adequate amount of polypeptide.

Covalent attachment of the polypeptide to a solid support may generally be achieved by first reacting the support with a bifunctional reagent that will react with both the support and a functional group, such as a hydroxyl or amino group, on the polypeptide.

The polypeptide may be fused with, or conjugated to, a tag that can be readily detected. The method employed for detecting the tag depends upon the nature of the tag. For example, scintillation counting or autoradiographic methods are generally appropriate for radioactive groups. Spectroscopic methods may be used to detect dyes, luminescent groups and fluorescent groups. Biotin may be detected using avidin, coupled to a reporter group (commonly a radioactive or fluorescent group or an enzyme).

To determine the presence or absence of a disorder characterized by an unwanted amount of phosphoinositide lipid, the signal detected in the assay is generally compared to a signal that corresponds to a predetermined cut-off value. In one preferred embodiment, the cut-off value is the average mean signal obtained when the polypeptide is incubated with samples from patients without the disorder. In general, a sample generating a signal that is three standard deviations above the predetermined cut-off value is considered positive for the disorder. Alternatively, the cut-off value may be determined using a Receiver Operator Curve, according to the method of Sackett et al., *Clinical Epidemiology: A Basic Science for Clinical Medicine*, Little Brown and Co., 1985, p. 106-7. Briefly, in this embodiment the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a disorder.

Those of skill in the art will appreciate that numerous other assay protocols exist that are suitable for use with the polypeptides disclosed herein. The above descriptions are intended to be exemplary only.

EXAMPLES

Experimental Protocol

1. Bacteria, *Dictyostelium*, Media and Growth Conditions

The *L. pneumophila* strains used in this study were wild-type strain JR32 (a salt-sensitive derivative of a streptomycin-resistant strain Philadelphia-1), the isogenic ΔicmT deletion mutant GS3011, which lacks a functional Icm/Dot T4SS, and corresponding strains constitutively producing the green fluorescent protein GFP or the red fluorescent protein DsRed-Express (Table 1). *L. pneumophila* was routinely grown for 3 days on CYE agar plates containing charcoal yeast extract, buffered with N-(2-acetamido)-2-aminoethanesulfonic acid (ACES) [41]. Liquid cultures were inoculated in AYE medium supplemented with BSA (0.5%) [42] at an $OD_{600}$ of 0.1 and grown for 21 h at 37° C. (post exponential growth phase). To maintain plasmids, chloramphenicol (cam) was added at 5 µg/ml. As "input" controls, 20 µl of a $10^5$/ml bacterial solution was plated and counted after 3 d incubation in all phagocytosis and intracellular growth experiments.

*Dictyostelium discoideum* wild-type strain Ax3 and the PI3K-1/2 double mutant (ΔPI3K1/2) were a gift from R. Firtel (University of California, San Diego, USA). The ΔPI3K1/2 mutant is lacking two PI3Ks which are related to the mammalian p110 catalytic subunit of class I PI3Ks. The mutant strain shows morphological, developmental and chemotactic phenotypes and is defective for vegetative growth in axenic medium and on bacterial lawns [34, 36, 38, 43]. Specifically, ΔPI3K1/2 is smaller than the isogenic wild-type strain and is impaired for (i) phagocytosis of live or autoclaved bacteria, (ii) pinocytosis of fluid markers, (iii) maturation of phagosomes to "spacious" phagosomes via homotypic fusion, and (iv) possibly exocytosis. A biochemical analysis of the phosphoinositide profile of ΔPI3K1/2 compared to the complemented strain revealed that the levels of $PI(3,4)P_2$ and $PI(3,4,5)P_3$ were reduced, while the level of PI(4)P was elevated, and PI(3)P as well as $PI(4,5)P_2$ remained unchanged [36].

*Dictyostelium* amoebae were grown axenically at 23° C. in 75 $cm^2$ tissue culture flasks in HL5 liquid medium (10 g glucose, 5 g yeast extract, 5 g proteose peptone, 5 g thiotone E peptone, 0.35 g $Na_2HPO_4$, 0.34 g $KH_2PO_4$ in 1 l $H_2O$, pH 6.5) supplemented with 10 µg/ml G418 or blasticidin-S when necessary. The amoebae were split once or twice a week and fed with fresh HL5 medium 24 h before use. For viability assays, *Dictyostelium* was plated together with *Klebsiella pneumoniae* on SM/5 agar plates, and plaque forming units (PFU) were counted after 3-4 d incubation at 23° C. [44].

2. Plasmid Construction, Protein Purification and Antibody Preparation

Translational gst fusions of sidC, sdcA, sidD and sdhB, were constructed by PCR amplification of the putative ORFs using the primers listed in Table 2. For sidD the ATG at position 120 downstream of a TTG in the ORF was used as a start codon. The PCR fragments were cut with BamHI and SalI and ligated into plasmid pGEX-4T-1 yielding pCR2, pCR16, pCR10, and pCR8, respectively (Table 1). All constructs were sequenced. Production of the fusion proteins in *E. coli* BL21(DE3) was induced at a cell density of $OD_{600}$ 0.6 with 0.5 mM isopropyl-1-thio-β-D-galactopyranoside (IPTG) for 3 h at 30° C. in LB medium. In all cases, this protocol resulted in a significant portion of soluble fusion protein of the expected size (132 kDa, 132 kDa, 79 kDa, 239 kDa, respectively). The fusion proteins were purified from lysates prepared by sonication using glutathione-sepharose beads in a batch procedure according to the manufacturer's recommendations (Amersham). Purity of the protein preparations was analyzed by SDS polyacrylamide gel electrophoresis.

According to a preferred embodiment GST-SidC was purified according to the following protocol:

1) Freshly transform *E. coli* BL21(DE3) with the GST-SidC fusion construct.

Streak on LB agar plates containing ampicillin (150 µg/ml) and incubate over night (o/n) at 37° C.

2) Wash the transformants with LB medium from the agar plate and inoculate 20 ml LB medium containing ampicillin (100 μg/ml). Incubate o/n (37° C.).
3) Inoculate 1 liter LB medium with 20 ml o/n culture (approximate $OD_{600}$ 0.05). Incubate at 37° C. (180 rpm) until $OD_{600}$ reaches approximately 0.5-0.8, preferably 0.6.
4) Chill liquid culture on ice (5 min), induce production of GST fusion protein with 0.5-1 mM isopropyl-1-thio-β-D-galactopyranoside (IPTG) for 3 h at 30° C. (180 rpm).

Under these conditions a significant portion of soluble fusion protein GST-SidC of the expected size of 132 kDa is produced.

5) Pellet bacteria, freeze pellet preferably in liquid nitrogen.
6) Cell lysis: Resuspend bacterial pellet in 30 ml cold PBS (80 g NaCl, 2 g KCl, 26.8 g $Na_2HPO_4 \times 7\ H_2O$, 2.4 g $KH_2PO_4$ per liter, adjust pH to 7.4 with HCl). Optional: add approximately 1 mg lysozyme (15 min). Add 50 μl 1M $MgCl_2$ and 1 mg DNAse. Pass the suspension 3×though a French Press (55 MPa). Centrifuge cell debris (2×15 min, 15'000 rpm, rotor SS34, 4° C.).
7) Incubate supernatant with glutathione-sepharose beads (Amersham Biosciences; 1.2 ml slurry, washed with 10 ml PBS, resuspended in 1 ml PBS) for 1-1.5 h on a wheel (20 rpm) at 4° C.
8) Wash 3× with 10 ml PBS (spin at approximately 550×g, 4° C.).
9) Elute with 1 ml elution buffer (0.462 g reduced glutathione, 700 μl 1 M Tris, pH 8.0, per 10 ml $H_2O$; final pH: 7.4-7.6).
10) Shock freeze aliquots.

The yield is approximately 15 mg purified protein per liter liquid culture grown in LB medium.

A translational his-sidC fusion was constructed by moving the sidC ORF (cut with BamHI and SalI) from pCR2 into pET28a(+), yielding pCR1. Production of $His_6$-SidC by *E. coli* BL21(DE3) was induced with 1 mM IPTG for 3-6 h at 30° C., resulting in a predominantly soluble protein of the expected size (109 kDa). The $His_6$-SidC fusion protein was purified by $Ni^{2+}$ affinity chromatography, and polyclonal antibodies against the purified protein were raised in rabbits (NeoMPS). The antibodies were affinity-purified from rabbit serum by using an Aekta liquid chromatography system (Amersham) and GST-SidC covalently linked to Affigel-10 beads (BioRad) [45]. Typical yield of purified anti SidC antibody was 2.2-3.2 mg/ml serum.

An *L. pneumophila* expression vector for M45-tagged SidC (pCR34) was constructed using pMMB207C [19] as a backbone. A ribosomal binding site (RBS) was introduced by moving an EcoRI/BamHI fragment from pUA26 [46] into pMMB207C, yielding pMMB207C-RBS-lcsC. To insert the DNA encoding the M45 tag, the oligos oCR-P1 and oCR-P2 harboring a mutation in the internal BamHI site of the M45 sequence (G to T in oligo oCR-P1) were used. The oligos were annealed (1 nmol each in 100 μl; heated to 94° C., followed by slow cooling to 4° C.) and ligated into pMMB207C-RBS-lcsC cut with NdeI and BamHI, yielding vector pMMB207C-RBS-M45. Finally, the fragment encoding SidC was moved from plasmid pCR2 into pMMB207C-RBS-M45 by using the BamHI and SalI restriction sites, yielding pCR34.

3. Analysis of Phagocytosis by Flow Cytometry

Phagocytosis of *L. pneumophila* by *Dictyostelium* was analyzed by flow cytometry using GFP-labeled bacteria. Exponentially growing *Dictyostelium* were seeded onto a 24-well plate ($5 \times 10^5$ cells/ml HL5 medium per well) and allowed to adhere for 1-2 h. *L. pneumophila* grown for 21 h in AYE liquid culture was centrifuged, resuspended in HL5 medium and used to infect the amoebae at a multiplicity (MOI) of 100 or at the MOI indicated ($OD_{600}$ of $0.3=2 \times 10^9$ bacteria/ml). The infection was synchronized by centrifugation (10 min at 880× g), infected cells were incubated at 25° C., and 30 min post-infection, extracellular bacteria were removed by washing three to five times with SorC (2 mM $Na_2HPO_4$, 15 mM $KH_2PO_4$, 50 μM $CaCl_2$, pH 6.0). Infected *Dictyostelium* were detached by vigorously pipetting, and $2 \times 10^4$ amoebae per sample were analyzed using a FACSCalibur flow cytometer (Becton Dickinson). The GFP fluorescence intensity falling into a *Dictyostelium* scatter gate was quantified using the FlowJo software (Treestar).

To confirm that the fluorescence observed arises from internalized and not from adherent *L. pneumophila*, phagocytosis was inhibited in parallel experiments. One h prior infection the medium was exchanged, and *Dictyostelium* was incubated in HL5 medium containing either latrunculin B (1-50 μM), cytochalasin A (1-50 μM) or, as a solvent control, DMSO (0.5%). Alternatively, the infection was performed on ice, and the infected cells were incubated at 4° C. While latrunculin B or cytochalasin A blocked phagocytosis in a dose-dependent manner, cytochalasin D (up to 50 μM), which effectively blocks macrophage phagocytosis, did not prevent uptake of *L. pneumophila* by *Dictyostelium* (data not shown).

In experiments addressing the role of PI3Ks, the amoebae were incubated in HL5 medium containing the PI3K inhibitors wortmannin (WM; 0.1-10 μM) or LY294002 (LY; 5-25 μM) for 1 h prior infection, which was then performed in presence of the inhibitors. At the concentrations indicated, the pharmacological inhibitors did not affect viability of *L. pneumophila* or *Dictyostelium*, as determined by measuring colony forming units (CFU) or PFU (data not shown).

4. Intracellular Growth of *L. pneumophila* within *Dictyostelium*

Release of *L. pneumophila* from *Dictyostelium* due to intracellular replication was quantified by determining CFUs in the supernatant as described [31, 33]. Briefly, exponentially growing *Dictyostelium* amoebae were washed with SorC and resuspended in MB medium (7 g yeast extract, 14 g thiotone E peptone, 20 mM MES in 1 l $H_2O$, pH 6.9). $10^5$ *Dictyostelium* cells per well were seeded onto a 96-well plate, let adhere for 1-2 h, and were infected at an MOI of 1 with *L. pneumophila* grown on CYE plates for 3-4 days and resuspended in MB medium. Occasionally, *L. pneumophila* grown in AYE medium for about 21 h was used as an inoculum. The infection was synchronized by centrifugation, and the infected amoebae were incubated at 25° C. At the time points indicated, the number of bacteria released into the supernatant was quantified by plating aliquots (10-20 μl) of appropriate dilutions on CYE plates. *L. pneumophila* did not grow in MB medium. Rather, the CFUs decreased 2-3 orders of magnitude within 3-6 days under these conditions (data not shown).

Intracellular bacterial growth before host cell lysis was quantified by counting CFU after selectively lysing infected *Dictyostelium* with saponin ("single round replication"). At the time points indicated, the MB medium was replaced by 100 μl 0.8% saponin and incubated for 15 min. The cells were lysed by pipetting, and aliquots were plated. Intracellular replication of GFP-labeled wild-type *L. pneumophila* or killing of GFP-labeled ΔicmT was also directly determined by flow cytometry. Here, the fluorescence intensity falling into a Dictyostelium scatter gate was quantified. Alternatively, the number of GFP-labeled L. pneumophila released into 120 µl Dictyostelium supernatant was quantified by flow cytometry using a scatter gate adjusted for bacteria.

To determine the effect of PI3K inhibitors on intracellular growth of L. pneumophila, Dictyostelium was incubated for 1 h in MB medium containing 5 µM wortmannin or 10-20 µM LY, respectively. The medium was not exchanged prior to an infection with L. pneumophila, leaving the inhibitors throughout the experiment. Since wortmannin is unstable in buffered aqueous solutions [47], LY was used preferentially. In some experiments, the inhibitors were added freshly to the medium every second day of the incubation period, yet, this protocol did not alter the results of the experiments. The PI3K inhibitors did not have an effect on L. pneumophila in MB medium (data not shown). Dictyostelium Ax3 wild-type cells treated with 5 µM wortmannin or 10 µM LY were as viable as untreated wild-type or ΔPI3K1/2 for up to 5 or 6 days in MB medium (data not shown). At later time points, cells treated with LY showed a reduced viability as determined by PFU on lawns of K. pneumoniae, and therefore, intracellular growth of L. pneumophila in presence of PI3K inhibitors was analyzed only up to 6 d.

5. Intracellular Trafficking of L. pneumophila

For immuno-fluorescence, Dictyostelium was split and fed two days prior to an experiment, seeded on sterile coverslips in 24-well plates at $2.5 \times 10^5$ per well in 0.5 ml HL5 medium and let grow over night. The medium was exchanged about 1 h before the infection and contained 20 µM LY where indicated. The L. pneumophila strains used for the infections were grown for 21 h ($OD_{600}$ of the inoculum: 0.1) in 3 ml AYE/BSA containing 5 µg/ml cam and 0.5 mM IPTG. Bacterial cultures were diluted in HL5 medium to a concentration of $5 \times 10^8$/ml, and 100 µl of the suspension were added to the amoebae (MOI=100). The infection was synchronized by centrifugation, and the cells were washed twice with HL5 medium.

At the time points indicated, the infected amoebae were washed 3 times with cold SorC buffer and fixed with 4% paraformaldehyde for 30 min at 4° C. The fixed cells were washed 3 times, permeabilized (0.1% Triton X-100, 10 min) and blocked with 2% normal human AB serum in SorC for 30 min. The coverslips were incubated for 1 h at room temperature on parafilm with 30 µl of primary antibodies diluted in blocking buffer (rhodamine-conjugated rabbit anti L. pneumophila Philadelphia-1 serogroup 1, 1:100 (m-Tech, Monoclonal Technologies); mouse anti M45 hybridoma supernatant, 1:4 [48]; affinity purified rabbit anti SidC (see above), 1:1000) and washed 3 times with blocking buffer after each antibody. Secondary antibodies were from Jackson Immuno Research Laboratories (FITC-conjugated goat anti mouse IgG, F(ab')$_2$-specific; Cy5-conjugated goat anti rabbit Fab fragment) and incubated at a 1:200 dilution in blocking buffer for 1 h at room temperature. Finally, DNA was stained with DAPI (1 µg/ml) in SorC for 5 min, the coverslips were washed twice and mounted using Vectashield (Vector Laboratories).

The samples were viewed with an inverted confocal microscope (Axiovert 200M; Zeiss), equipped with a 100×oil phase contrast objective (Plan Neofluar; Zeiss), an "Ultraview" confocal head (Perkin Elmer) and a krypton/argon laser (643-RYB-A01; Melles Griot). Data processing and three-dimensional reconstruction was performed with the "Volocity" 2.6.1 software (Improvision).

The amount of SidC on LCVs harboring DsRed-labeled L. pneumophila in calnexin-GFP-labeled wild-type Dictyostelium (untreated or treated with 20 µM LY) or in ΔPI3K1/2 was quantified by immuno-fluorescence using affinity purified anti SidC and Cy5-conjugated secondary antibodies. The fluorescence intensity of an area identical for all samples and covering the LCV was quantified using the "Quantity One" software (BioRad) after background correction (averaged intensity of 3 areas within the infected amoeba). To standardize the procedure, all images were acquired with the same exposure time, only LCVs containing rod-shaped and non-permeabilized bacteria were considered, and "equatorial" sections along the z-axis through the bacteria were chosen.

6. Binding of Icm/Dot-Secreted L. pneumophila Proteins to Phosphoinositides and Other Lipids in vitro Direct binding of L. pneumophila Icm/Dot-secreted putative effector proteins to phosphoinositides and other lipids was tested in a protein-lipid overlay assay [49]. The lipid compounds bound to nitrocellulose membranes were incubated with GST-effector fusion proteins, which were constructed and purified as described above. Preliminary binding experiments were performed using synthetic di-hexadecanoyl-phosphoinositides (Echelon) or purified authentic di-acyl- (preferentially 1-stearoyl-2-arachidonoyl) phosphoinositides (Sigma; Matreya LLC). 3 µl of diluted stock solutions in $CHCl_3$:MeOH:$H_2O$=1:2:0.8 (synthetic phosphoinositides) or MeOH (authentic phosphoinositides) were spotted onto nitrocellulose membranes yielding 6-200 pmol per spot. The membranes were blocked with 4% fat free milk powder in TBST (50 mM Tris, 150 mM NaCl, 0.1% Tween-20 (v/v), pH 8.0) for 1 h at room temperature and incubated with the fusion proteins (ca. 120 pmol/ml blocking buffer) over night at 4° C. Binding of the GST-effector fusion proteins to lipids was visualized by ECL (Amersham) using a monoclonal anti GST antibody (Sigma) and a secondary goat anti mouse peroxidase-labeled antibody (Sigma). The final experiments were done with commercially available PIP-strips™ and PIP-arrays™ (Echelon), using GST-tagged PH domains of PLCδ1 (PIP$_2$ Grip™) and LL5α (MultiPIP GriP™) as control reagents for the presence of PI(4,5)P2 or all phosphoinositides on the nitrocellulose membranes.

To test whether SidC binds to phosphoinositides incorporated into phospholipid (PL) vesicles, we used affinity purified GST-SidC or GST-SidD and biotinylated PL vesicles (1 mM lipid) composed of 65% phosphatidylcholine (PC), 29% phophatidylethanolamine (PE), 1% biotinylated PE and 5% either PI(4)P, PI(3)P or PI(4,5)P$_2$ (PolyPIPosomes™; Echelon). The PL vesicles (20 µl, 1 nmol PI) were incubated for 20 min at 4° C. with GST-SidC or GST-SidD fusion proteins (40 pmol) in a total of 1 ml binding buffer (50 mM Tris, 150 mM NaCl, 0.05% Nonidet P40, pH 7.6). The liposomes were subsequently centrifuged (10 min, 20'800×g) and washed 5 times with 1 ml binding buffer. Finally, the pellet was resuspended in 25 µl SDS PAGE loading buffer, boiled and loaded onto an 8% SDS gel. GST fusion proteins were visualized by Western blot with a monoclonal anti GST antibody (Sigma).

7. Accession Numbers

The GenBank accession numbers for the proteins mentioned in this application are Dictyostelium calnexin, AF073837; Dictyostelium PI3K1 and PI3K2, U23476 and U23477, respectively; human FAPP1, AF286162; L. pneumophila Icm/Dot T4SS conjugation apparatus, Y15044; SidC, AY504673 (DNA sequence provided in FIG. 9; SEQ ID NO: 3) SidC paralog SdcA, AY504674 (DNA sequence provided in FIG. 10; SEQ ID NO: 4); LepA, AAP20592 (FIG. 11; SEQ ID NO: 5); LepB, AAP20593 (FIG. 12; SEQ ID NO: 6); LidA, AA061471 (FIG. 13; SEQ ID NO: 7); LPG 2311, AAU28373 (FIG. 14; SEQ ID NO: 8).

8. Strains, Plasmids, Oligonucleotides

TABLE 1

Strains and plasmids.

| Name | Relevant characteristics | References |
|---|---|---|
| Strains | | |
| *L. pneumophila* | | |
| JR32 | Salt-sensitive derivative of virulent *L. pneumophila* Philadelphia-1 serogroup 1 | [50] |
| GS3011 | JR32 icmT3011::Kan$^R$ | [51] |
| *E. coli* | | |
| TOP10 | | Invitrogen |
| BL21(DE3) | | Novagen |
| *Dictyostelium* | | |
| Ax3 | Wild-type | [34] |
| ΔPI3K1/2 | Ax3 ΔPI3K1/2 | [34] |
| Ax2 | Wild-type | [52] |
| HG1769 | Ax2 Δcalreticulin, blasticidin-S$^R$ (Bls$^R$) | [52] |
| HG1770 | Ax2 Δcalnexin, Bls$^R$ | [52] |
| HG1773 | Ax2 Δcalnexin/calreticulin, Bls$^R$, G418$^R$ | [52] |
| Plasmids | | |
| pCR1 | sidC-his in pET28a(+) | This study |
| pCR2 | sidC-gst in pGEX-4T-1 | This study |
| pCR8 | sdhB-gst in pGEX-4T-1 | This study |
| pCR10 | sidD-gst (120ATG) in pGEX-4T-1 | This study |
| pCR16 | sdcA-gst in pGEX-4T-1 | This study |
| pCR33 | pMMB207C-RBS-M45, from pMMB207C-RBS-lcsC | This study |
| pCR34 | pMMB207C-RBS-M45-SidC | This study |
| pET28A(+) | expression of N-terminal his fusions; P$_{T7}$; Kan$^R$ | Novagen |
| pGEX-4T-1 | expression of N-terminal gst fusions; P$_{tac}$; Amp$^R$ | Amersham |
| pMMB207C | *Legionella* expression vector, ΔmobA, no RBS | [19] |
| pMMB207-Km14-gfp$_c$ | pMMB207-Km14, ΔlacI$^q$, constitutive gfp | [53] |
| pMMB207-RBS-lcsC | expression vector for lcsC, RBS (= pUA26) | [46] |
| pMMB207C-RBS-lcsC | expression vector for lcsC, RBS, ΔmobA | This study |
| pMMB207C-RBS-M45 | expression vector, ΔmobA, RBS, M45-(Gly)$_5$ | This study |
| pSW001 | pMMB207C, ΔlacI$^q$, constitutive dsred | [53] |
| pCalnexin-GFP | act15/calnexinA-RSSSKLK-gfp(S65T), G418$^R$ | [52] |

TABLE 2

Oligonucleotides.

| Oligo-nucleotides | Relevant characteristics or sequence$^a$ | Comments |
|---|---|---|
| oCR1 | AAAAACGC<u>GGATCC</u>ATGGTGATAAACATGGT TGACG (SEQ ID NO:9) | 5' sidC; BamHI |
| oCR2 | AAAAACGC<u>GTCGAC</u>CTATTTCTTTATAATTC CCGTGTAC (SEQ ID NO:10) | 3' sidC; SalI |
| oCR4 | AAAAACGC<u>GTCGAC</u>TTAAATAGTAAGACTCG AGTTAG (SEQ ID NO:11) | 3' sidD; SalI |
| oCR7 | AAAAACGC<u>GTCGAC</u>TCATGCTACTATTAAGC ATAGAGG (SEQ ID NO:12) | 5' sdhB; SalI |
| oCR8 | AAAAGAAT<u>GCGGCCGC</u>TTACAATTTGGTAAA TTCGATTTCAC (SEQ ID NO:13) | 3' sdhB; NotI |
| oCR13 | AAAAACGC<u>GGATCC</u>ATGCGTTCGATTATTAC ACAAATC (SEQ ID NO:14) | 5' sidD, BamHI |
| oCR29 | AAAAACGC<u>GTCGAC</u>TCATGAACATGGTTGAC AAAATAAAATTC (SEQ ID NO:15) | 5' sdcA; SalI |
| oCR30 | AAAAGAAT<u>GCGGCCGC</u>CTATATTGTATTCCT AACAGTTTCTC (SEQ ID NO:16) | 3' sdcA; NotI |
| oCR-P1 | <u>TATGG</u>CCATGGATCGGAGTAGGGATCGCCTA CCTCCTTTTGAGACAGAGACGCGTATCCTCG GTGGTGGTGGTG (SEQ ID NO:17) | 'NdeI, BamHI' |
| oCR-P2 | <u>GATCC</u>ACCACCACCACCACCGAGGATACGCG TCTCTGTCTCAAAAGGAGGTAGGCGATCCCT ACTCCGATCCATGGC<u>CA</u> (SEQ ID NO:18) | 'BamHI, NdeI' |

$^a$Restriction sites are underlined.

Results

1. PI3Ks are Dispensable for Phagocytosis of Wild-Type *L. pneumophila*

Phagocytosis of *L. pneumophila* by *Dictyostelium* was quantified by flow cytometry using bacteria constitutively expressing gfp. About 10 times more amoebae showed increased fluorescence, if infected with wild-type *L. pneumophila* compared to an icmT mutant strain (ΔicmT), which lacks a functional Icm/Dot T4SS (FIG. 1). This assay indicates that at least 10 times more wild-type *L. pneumophila* were phagocytosed compared to ΔicmT. Icm/Dot-dependent phagocytosis was observed at a multiplicity of infection (MOI) ranging from 1 to 100 and blocked by inhibitors of actin polymerization (latrunculin B, 20 μM; cytochalasin A, 10 μM), or by performing the infection at 4° C.

Wild-type *L. pneumophila* was only slightly less efficiently phagocytosed by *Dictyostelium* ΔPI3K1/2 (−4%), or wild-type *Dictyostelium* treated with the PI3K inhibitors wortmannin (WM; −19%) or LY294002 (LY; −33%), respectively (FIG. 2A, data not shown). Thus, genetic and pharmacological data indicate that phagocytosis of *L. pneumophila* by *Dictyostelium* does not require PI3Ks. This result is in agreement with the finding that uptake of *L. pneumophila* by macrophage-like cells occurs via a wortmannin-insensitive pathway [35]. Contrarily, phagocytosis of ΔicmT was reduced by 77-88% upon deletion or inhibition of PI3Ks, corresponding to reports that *Dictyostelium* PI3K1/2 is involved in phagocytosis of *E. coli* [36]. The addition of PI3K inhibitors to ΔPI3K1/2 did not further diminish phagocytosis of ΔicmT, indicating that other *Dictyostelium* class I PI3Ks present in the genome [37] are not involved in uptake.

Figure 3:
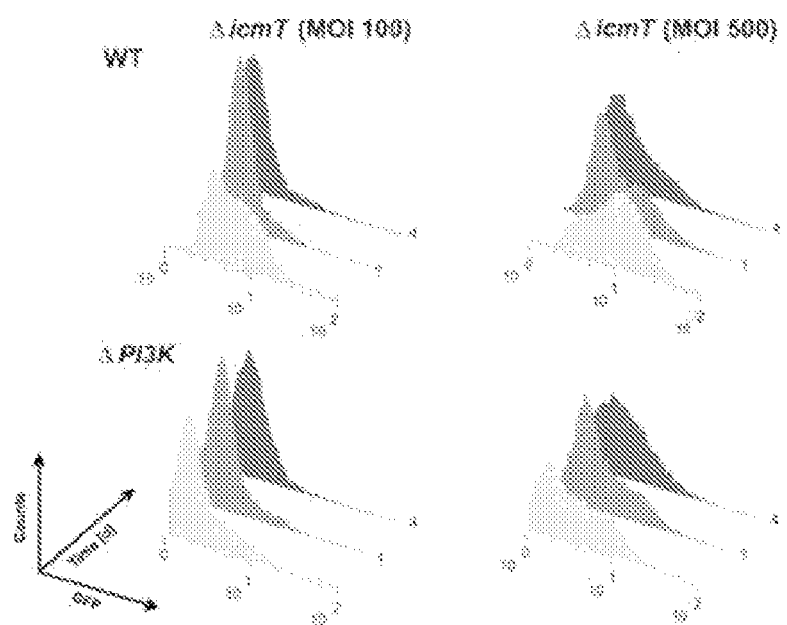

2. PI3Ks are Involved in Intracellular Replication of Wild-Type *L. pneumophila* and Degradation of ΔicmT The effect of PI3Ks on intracellular replication of *L. pneumophila* was quantified by determining colony forming units (CFUs) in the supernatant of infected *Dictyostelium* cultures. Compared to wild-type *Dictyostelium*, about a factor of 100 more wild-type *L. pneumophila* were released within 6-8 days from ΔPI3K1/2 (FIG. 2B) or amoebae treated with LY (FIG. 2C), indicating that functional PI3Ks restrict intracellular replication of *L. pneumophila*. To test intracellular growth of *L. pneumophila* more directly, we analyzed *Dictyostelium* infected with GFP-labeled *L. pneumophila* by flow cytometry (FIG. 2D). In this assay, GFP-labeled *L. pneumophila* grew earlier and more efficiently within ΔPI3K1/2 or wild-type *Dictyostelium* treated with LY compared to untreated wild-type amoebae. Treatment of ΔPI3K1/2 with LY did not enhance intracellular replication further, suggesting that no other class I PI3Ks are involved. Quantification by flow cytometry of GFP-labeled wild-type *L. pneumophila* released from *Dictyostelium* showed that *L. pneumophila* emerged earlier from *Dictyostelium* lacking PI3Ks, yet apparently grew with similar rates (data not shown). In a "single round" growth assay, where the amoebae were selectively lysed with saponin, *L. pneumophila* started to grow already after 1 d in absence of PI3Ks, while in wild-type *Dictyostelium* the numbers of wild-type *L. pneumophila* initially decreased (data not shown). Finally, while ΔicmT did not replicate within *Dictyostelium* in presence or absence of PI3Ks (FIG. 2B), the mutant bacteria were killed about 2 times slower within ΔPI3K1/2 (FIG. 3, data not shown). These results are in agreement with a requirement of class I PI3Ks for the endocytic degradative pathway [23].

3. Trafficking of *L. pneumophila* is Altered in Absence of Functional PI3Ks

The finding that *L. pneumophila* replicates more efficiently in absence of PI3Ks suggests that vesicle trafficking and formation of the LCV is altered. As a marker for LCVs, we used the ER membrane protein calnexin-GFP, which within 2 h co-localizes with about 65% LCVs harboring wild-type *L. pneumophila* but not at all with ΔicmT-containing LCVs (data not shown; [6, 9]). Calnexin does not profoundly affect trafficking of *L. pneumophila*, since intracellular replication within wild-type *Dictyostelium* was similar to replication in *Dictyostelium* mutants lacking calnexin, calreticulin, calnexin/calreticulin, or in a calnexin-GFP-expressing strain (data not shown).

In Dictyostelium wild-type and in strains lacking PI3Ks, the LCVs acquired calnexin-GFP with similar kinetics (data not shown), suggesting that initial docking and fusion of ER-derived vesicles with the *Legionella* phagosome is not affected by PI3Ks. However, the morphological dynamic of the LCV was altered, as the transition from tight to spacious vacuoles was severely impaired in *Dictyostelium* lacking functional PI3Ks (FIG. 4A). In wild-type *Dictyostelium*, 25% of the LCVs appeared spacious as early as 15 min post infection, and within 2 h, 40% spacious vacuoles were scored (FIG. 4B). In contrast, in *Dictyostelium* lacking PI3Ks, the portion of spacious LCVs was less than 5% at 15 min post infection, reached within 2 h only 10% (ΔPI3K1/2) or 20% (LY-treated wild-type *Dictyostelium*), and remained below the level observed in wild-type *Dictyostelium* throughout the 6 h observation period. At later time points, scoring of the vacuoles became difficult, since infected *Dictyostelium* easily detached from the substratum, and LCVs harboring replicating bacteria appeared spacious in presence or absence of PI3Ks. In summary, these results indicate that class I PI3Ks play a role in the modulation of the LCV and the formation of a replication-permissive vacuole.

4. The Icm/Dot-Secreted *L. pneumophila* Protein SidC Localizes to Tight and Spacious Vacuoles To correlate the morphology of the LCV with the presence of a putative *L. pneumophila* effector protein, we stained for the Icm/Dot-secreted protein SidC ("Substrate of Icm/Dot transporter", [18]). The function of SidC is unknown. However, the protein localizes to LCVs in *Legionella*-infected macrophages and is exposed to the cytoplasmic side of the vacuolar membrane. Immuno-staining of M45-tagged SidC within *Legionella*-infected *Dictyostelium* amoebae revealed its presence on tight as well as spacious LCVs (FIG. 4C). Similar to LCVs labeled with calnexin-GFP, the majority of M45-SidC-labeled LCVs formed in wild-type *Dictyostelium* after 75 min appeared spacious, while at the same time the LCVs in ΔPI3K1/2 were all tight-fitting (data not shown). Some punctate background staining was also visible in uninfected *Dictyostelium* and thus is not due to association of SidC with cellular organelles. As even upon overexpression, M45-tagged SidC localized exclusively to the LCV, but not to other cellular vesicles, SidC anchors with high affinity and specificity to the LCV membrane.

5. SidC and SdcA Directly and Specifically Bind to PI(4) Phosphate in vitro

Intracellular replication of *L. pneumophila* depends on phosphoinositide metabolism as well as on the Icm/Dot T4SS. A direct link between these host cell and pathogen factors would exist, if secreted *L. pneumophila* proteins bind to phosphoinositides on the LCV. SidC is an attractive candidate to test this hypothesis, since the protein binds to the LCV membrane, yet no transmembrane helices are predicted from its primary sequence. To determine whether SidC interacts with phosphoinositides in vitro, we assayed binding of an N-terminal GST-SidC fusion protein to phosphoinositides and other lipids immobilized on nitrocellulose membranes. Under these conditions, SidC directly and almost exclusively bound to PI(4)P and to a much weaker extent to PI(3)P but not to other phosphoinositides or lipids (FIG. 5A). Estimated from binding of SidC to phosphoinositides arrayed in twofold serial dilutions, the affinity of SidC for PI(4)P was a factor of 50-100 higher than for PI(3)P. The SidC paralogue SdcA (72% identity on an amino acid level) also specifically bound to PI(4)P and PI(3)P, yet compared to SidC with apparently lower affinity to PI(4)P and higher affinity to PI(3)P.

We also tested GST fusion proteins of SidD and SdhB for binding to phosphoinositides (FIG. 5A). SdhB is a paralogue of SidH and predicted with low stringency by the "scansite" algorithm (available from the Massachusetts Institute of Technology) to contain an ANTH domain putatively binding PI(4,5)P$_2$. While the GST-SidD fusion protein did not bind to any of the lipids tested in vitro, the GST-SdhB fusion protein bound very weakly only to PI(3)P but not to other lipids.

To investigate the binding specificity of SidC to phosphoinositides incorporated into phospholipid (PL) vesicles, we incubated GST-SidC with PL vesicles composed of phosphatidylcholine (65%), phosphatidylethanolamine (30%), and 5% either PI(4)P, PI(3)P or PI(4,5)P$_2$. GST-SidD was used as a putative negative control. The PL vesicles were incubated with GST-SidC or GST-SidD, centrifuged and washed several times, prior to analyzing binding of the proteins by Western blot with an anti GST antibody (FIG. 5B). Under the conditions used, SidC almost exclusively bound to PI(4)P, while binding to PI(3)P was negligible. Binding of SidC to PI(4,5)P$_2$ was in the range observed for SidD and thus considered unspecific. Estimated by densitometry, about 200 times more SidC bound to PL vesicles harboring PI(4)P compared to vesicles containing PI(3)P or PI(4,5)P$_2$. Taken together, using two different biochemical assays SidC was found to specifically bind to PI(4)P in vitro.

6. SidC Preferentially Binds to LCVs in Absence of Functional PI3Ks

Figures 6A, 6B:
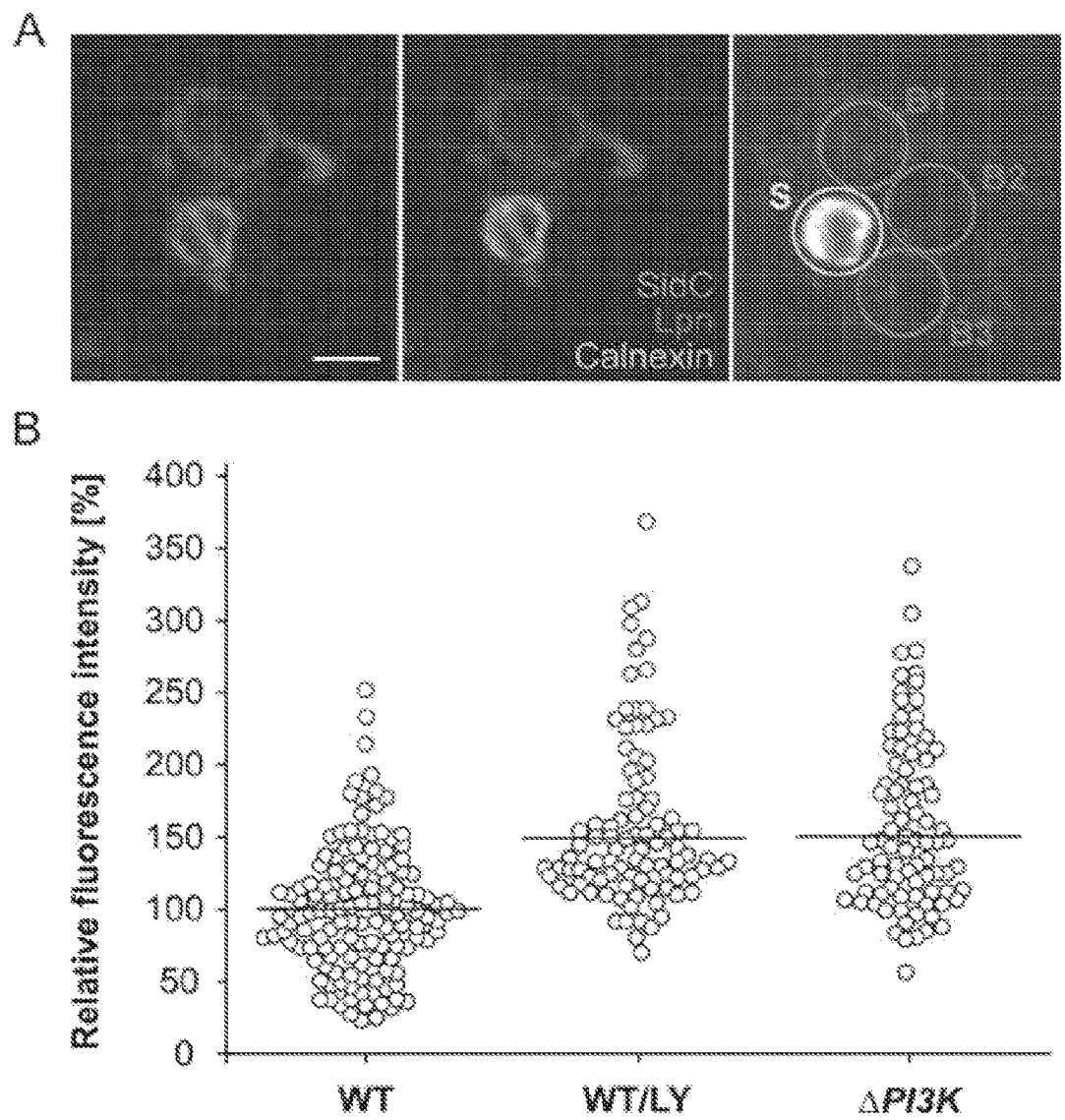

To address the question of whether SidC binds to PI(4)P on LCVs in infected Dictyostelium amoebae, we determined whether altering the ratio of cellular phosphoinositides affects the amount of SidC bound to LCVs. In Dictyostelium ΔPI3K1/2 the level of the PI3K products PI(3,4)P$_2$ and PI(3,4,5)P$_3$ is decreased, while the level of the PI3K substrate PI(4)P is increased compared to the complemented strain [36]. Accordingly, if the level of phosphoinositides on LCVs mirrors the cellular phosphoinositide levels, SidC is predicted to preferentially bind to LCVs in absence of PI3Ks. To test whether PI3Ks affect the amount of SidC on LCVs, SidC bound to LCVs was quantified by immuno-fluorescence using an affinity purified antibody (FIG. 6A). SidC and calnexin-GFP always and strictly co-localized on LCVs regardless of whether PI3Ks were present or not. We found that with high statistical significance (p<10$^{-9}$) about a factor of 1.5 more SidC localized to LCV membranes in wild-type Dictyostelium treated with LY or ΔPI3K1/2, compared to LCVs formed in wild-type Dictyostelium (FIG. 6B). This result is in agreement with the notion that in absence of functional PI3Ks the amount of cellular and vacuolar PI(4)P is increased, allowing more SidC to bind to the LCV in L. pneumophila-infected host cells.

7. PI(4)P is a Lipid Marker of LCVs Harboring Icm/Dot-Proficient L. pneumophila

Figure 7A:
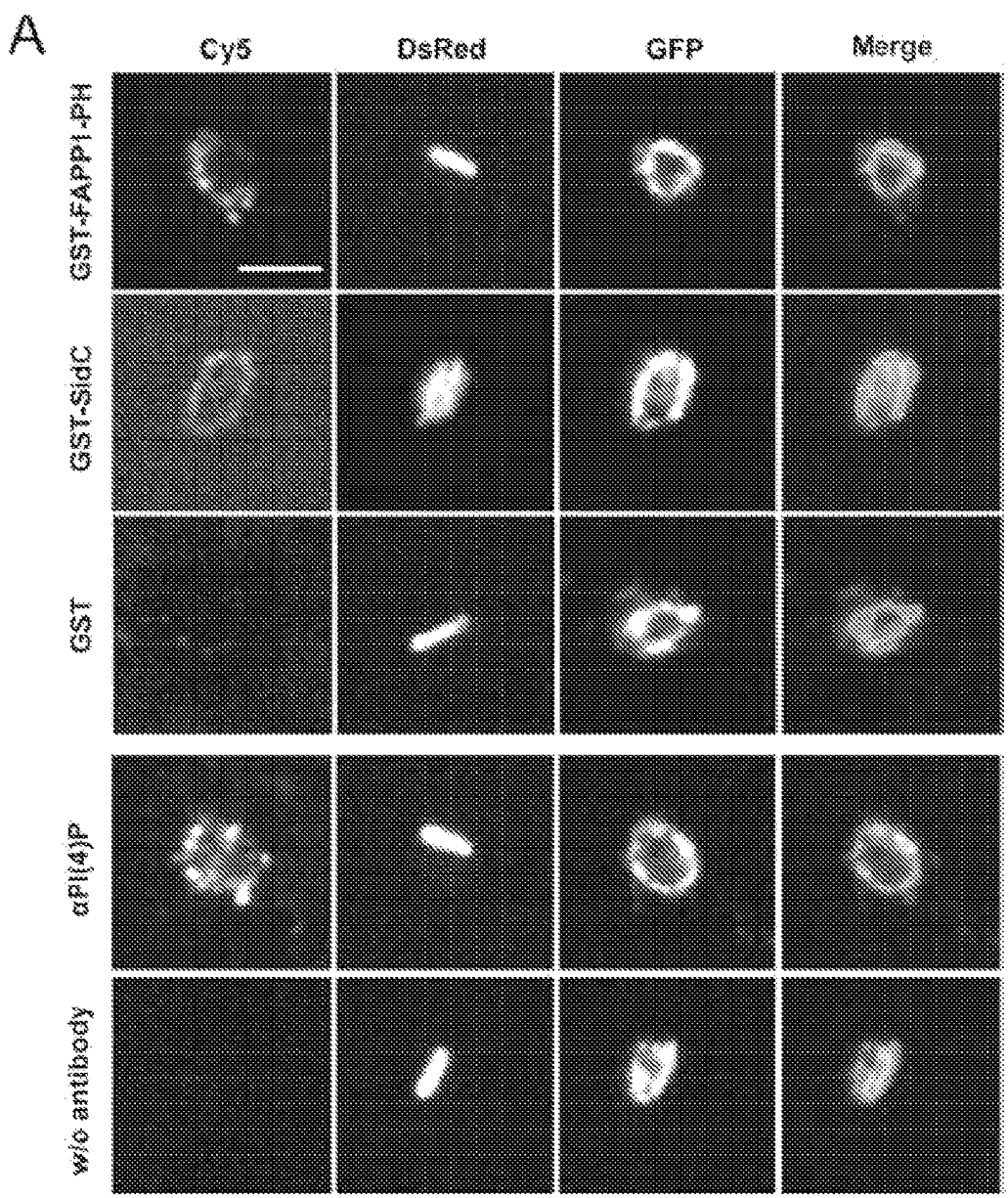

SidC specifically binds to PI(4)P in vitro and to the membrane of the LCV, suggesting that PI(4)P is a constituent of the LCV. To test whether PI(4)P is indeed a lipid marker of the LCV, we used as probes a PI(4)P-specific antibody or the PH domain of FAPP1 (phosphatidylinositol(4) phosphate adaptor protein-1) fused to GST. FAPP1 is required for transport from the trans Golgi network to the plasma membrane and has been shown to specifically bind PI(4)P [49,54]. The PI(4)P-specific antibody, as well as the GST FAPP1-PH probe, labeled calnexin-GFP-positive LCVs in homogenates of Dictyostelium infected with L. pneumophila (FIG. 7A). Similarly, GST-SidC stained the LCV in homogenates of L. pneumophila-infected Dictyostelium. Using the PI(4)P-specific antibody, we found that 80% of calnexin-GFP-positive, wild-type L. pneumophila-containing vacuoles stain positive for PI(4)P. Omission of the anti-PI(4)P antibody or using GST alone did not label the LCV. These results establish PI(4)P as a lipid marker of the LCV in L. pneumophila infected Dictyostelium. In intact calnexin-GFP-labeled Dictyostelium infected with L. pneumophila, the PI(4)P probes produced a punctate staining on the cytoplasmic membrane and in the cytoplasm, rendering it difficult to detect PI(4)P on the LCVs (unpublished data).

Figure 7B:
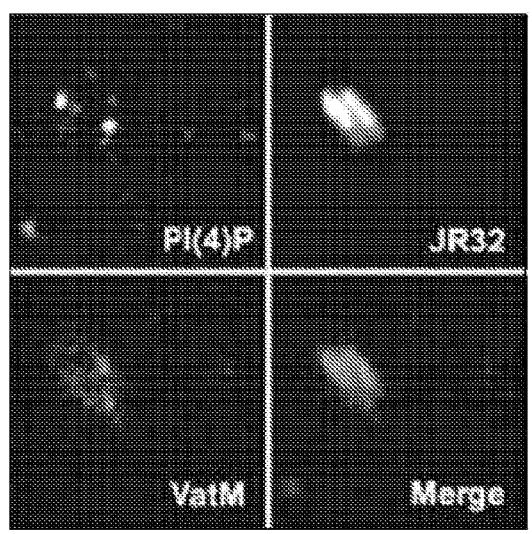
Figure 7C:
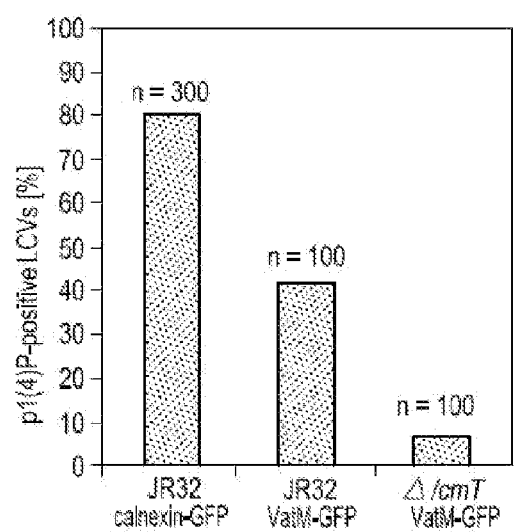

To address the question of whether the presence of PI(4)P on LCVs is dependent on the Icm/Dot T4SS, we used the Dictyostelium wild-type strain Ax3 expressing VatM-GFP. VatM is the 100-kDa transmembrane subunit of the vacuolar H$^+$-translocating adenosine triphosphatase (V-ATPase), which is excluded from LCVs harboring wild-type L. pneumophila but is delivered to LCVs containing ΔicmT by fusion with endolysosomes [9,19]. One hour post-infection, only 15% of wildtype but 41% of ΔicmT mutant L. pneumophila resided in vacuoles staining positive for VatM-GFP. Interestingly, however, 42% of the VatM-GFP-positive LCVs harboring wildtype L. pneumophila stained positive for PI(4)P, compared to only 6% of VatM-positive LCVs containing ΔicmT (FIGS. 7B and 7C). These results indicate that the presence of PI(4)P on LCVs is Icm/Dot-dependent.

Figure 7D:
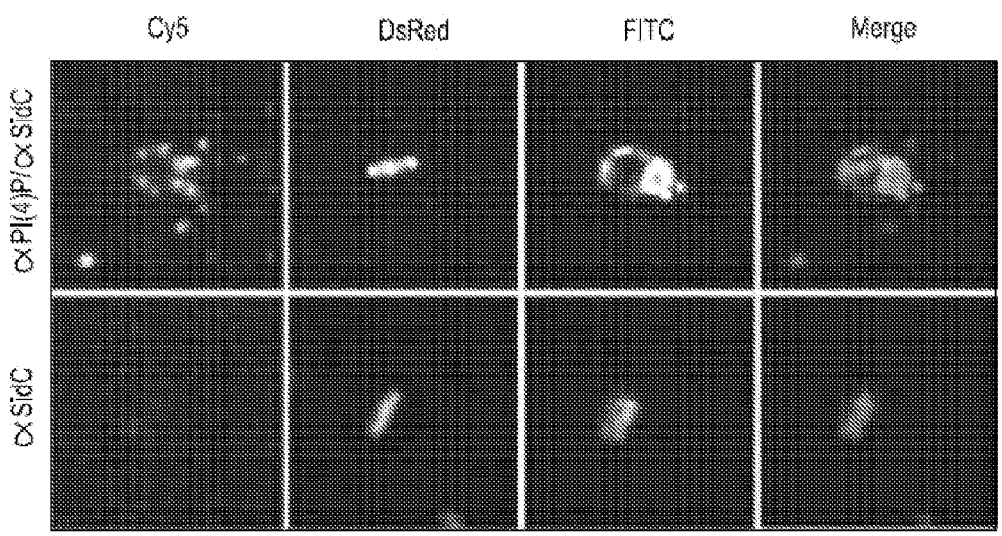

The mechanism of intracellular replication of L. pneumophila within amoebae and macrophages appears to be very similar. To test whether LCVs formed in macrophages also contain PI(4)P, we used RAW264.7 cells. L. pneumophila grows within these macrophages [1,46] and therefore the corresponding LCVs represent replication-permissive compartments. In lysates of RAW264.7 macrophages infected with L. pneumophila, the LCVs were labeled by an anti-PI (4)P antibody as well as by an anti-SidC antibody (FIG. 7D). As expected, upon omission of the anti-PI(4)P antibody, only SidC was detected on the LCV. These results demonstrate that PI(4)P is also a lipid component of the LCV in macrophages, and the results further underscore the structural similarity of LCVs within amoebae and macrophages. Similar to Dictyostelium, in intact L. pneumophila-infected macrophages, the PI(4)P probes led to a punctate staining pattern on the cytoplasmic membrane and in the cytoplasm.

8. Fragments of SidC Directly and Specifically Bind to PI(4) Phosphate

The L. pneumophila SidC protein (105 kDa) as shown in FIG. 5E specifically binds PI(4)P. Smaller, C-terminal fragments of SidC (SidC__3C: 36 kDa, SidC__3-4: 20 kDa; FIG. 5E) bind PI(4)P with the same specificity (FIG. 5F).

According to preferred embodiments of the present invention, the segments comprise the following amino acid sequences:

```
SidC-3-4 (169 AA) (SEQ ID NO: 1):
SKYSSKPLLDVELNKIAEGLELTAKIYNEKRGREWWFKGSRNEARKTQCE

ELQRVSKEINTLLQSESLTKSQVLEKVLNSIETLDKIDRDISAESNWFQS

TLQKEVRLFRDQLKDICQLDKYAFKSTKLDEIISLEMEEQFQKIQDPAVQ

QIVRDLPSHCHNDEAIEFF

SdcA-3-4 (168 AA) (SEQ ID NO: 2):
SKYSSKPLLDVELNKIAEGLDLTAKIYNEKRKSEWFKGSRNEARKTQCEE

LQRVSQEINALLQSESLTKSQVLEKVLNSIEALDKIDRDISAEYNLFKST
```

```
-continued
LQKEVQSFRDQLKDICQLDNYAFKSTKLDEIISLEMEEQFQMIKDPAVQQ

IVRDLPSHCHNNEVIEFF
```

The SidC-3-4 and SdcA-3-4 sequences are 90.5% identical (ClustalW algorithm).

Similar to full length SidC, the fragments are stable and robustly bind PI(4)P even after cycles of shock freezing and thawing. The proteins lose their PI(4)P-binding activity upon freezing at −20° C. 25-100 μg of the affinity purified GST fusion protein is routinely used per protein-lipid overlay assay. These features allow the use of SidC- or SdcA-fragments as specific probes for PI(4)P in cell biological and biochemical assays.

To produce the SidC-derived PI(4)P-binding proteins, translational GST fusions were constructed by PCR amplification. All constructs were sequenced. The following preferred constructs are provided to produce recombinant SidC-derived PI(4)P-binding GST fusion proteins:

pGEX-4T-1-SidC
pGEX-4T-1-SidC_3C
pGEX-4T-1-SidC_3-4

9. Applications of the PI(4)P-Binding Proteins SidC and SdcA and Fragments Thereof SidC, SdcA and peptide fragments thereof may be employed as probes in biochemical assays as well as in cell biological assays to detect and quantify PI(4)P. The probes are either recombinant tagged proteins, which are purified and can be used in a soluble form or immobilized on surfaces, or ectopically expressed fusion proteins (Table 3).

The information disclosed above allows the person skilled in the art to perform, for example, the following diagnostic and analytic applications:

Diagnostic assays to detect and quantify PI(4)P in biological samples.
Analytic assays to stain and quantify PI(4)P in sub-cellular compartments of cells.
Assays for phosphoinositide kinases or phosphatases which turn over or produce radio- or fluorescence-labeled PI(4)P. Screens for enzyme inhibitors or agonists.
Lipid-protein overlay or pull-down assays using phosphoinositides immobilized on membranes or beads.
Pull down assays to enrich PI(4)P-containing cellular compartments and lipid vesicles.
Fusion assays using PI(4)P-containing liposomes.

| Tag | Detection |
|---|---|
| None | Antibody (against SidC) |
| GST, M45, Myc, HA, His, etc | Antibody (against tag) |
| Fluorescent proteins (GFP, etc) | Fluorescence |
| Fluorophores (FITC, etc) | Fluorescence |
| Biotin | Avidin-peroxidase, Avidin-fluorophor |
| Colloidal gold | Electron microscopy |

Table 3. Examples of detectable tags fused or conjugated to SidC/SdcA or their PI(4)P-binding domains.

SidC, SdcA and PI(4)P-binding peptide fragments thereof interfere with phosphoinositide-dependent vesicle trafficking and are advantageously used to modulate such trafficking processes, which are impaired under certain pathological conditions.

The therapeutic applications include:
Ectopical or retroviral expression of SidC/SdcA or fragments derived thereof.
Delivery of purified recombinant PI(4)P-binding SidC/SdcA-derived peptides.

10. Other *L. pneumophila* Effector Proteins Binding to Phosphoinositides

In our attempts to systematically screen secreted *L. pneumophila* proteins for binding to phosphoinositides, we identified the Icm/Dot-secreted effectors LepA and LepB [19], LidA [17], as well as the putative Icm/Dot substrate Lpg2311 [39] as candidate proteins binding to mono-phosphorylated phosphoinositides (FIG. 5C, 5D). Given the large number of Icm/Dot-secreted proteins, we expect further phosphoinositide-binding *L. pneumophila* proteins to be identified.

11. Other *L. pneumophila* Effectors Interfering with Phosophoinositide Metabolism Several lines of evidence show that in addition to the effectors identified above, other *L. pneumophila* proteins also interfere with host cell phosphoinositide metabolism:

(i) The modulation of phosphoinositide metabolism has profound effects on intracellular replication of *L. pneumophila*, yet a sidC-sdcA double mutant is not impaired for intracellular replication. Therefore, other phosphoinositide-binding effector proteins might have redundant functions.

(ii) While PI3Ks are required for phagocytosis of an *L. pneumophila* ΔicmT mutant strain lacking a functional Icm/Dot T4SS, wild-type *L. pneumophila* is phagocytosed one order of magnitude more efficiently than ΔicmT and independently of PI3Ks. These findings suggest that wild-type *L. pneumophila* bypasses a requirement for PI3Ks by actively modulating phosphoinositide metabolism of the host cell.

(iii) Experiments performed with *Dictyostelium* PI(5)P phosphatase mutant strains revealed that *L. pneumophila* grows 2-3 orders of magnitude more efficiently in a strain lacking PI(5)P phosphatase-4 (PI5P-4), compared to wild-type *Dictyostelium* or other PI(5)P phosphatase mutants (FIG. 8). *Dictyostelium* PI5P-4 contains a functionally important RhoGAP domain and is the homologue of human PI(5)P phosphatase OCRL-1, which is implicated in the severe disease oculocerebrorenal syndrome of Lowe [55]. OCRL-1 localizes to the trans Golgi network (TGN) and likely regulates bidirectional endosome to TGN trafficking as well as actin dynamics. In absence of PI5P-4, the amount of its substrates PI(4,5)P2 and PI(3,4,5)P3 is increased, indicating that *L. pneumophila* effectors also interact with poly-phosphorylated phosphoinositides.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

REFERENCES

1. Fields, B. S., The molecular ecology of Legionellae. Trends Microbiol, 1996. 4: 286-290.F
2. McDade, J. E., et al., Legionnaires' disease: isolation of a bacterium and demonstration of its role in other respiratory disease. N Engl J Med, 1977. 297: 1197-203.
3. Nash, T. W., D. M. Libby, and M. A. Horwitz, Interaction between the Legionnaires' disease bacterium (*Legionella pneumophila*) and human alveolar macrophages. Influence of antibody, lymphokines, and hydrocortisone. J Clin Invest, 1984. 74: 771-782.

4. Horwitz, M. A., The Legionnaires' disease bacterium (*Legionella pneumophila*) inhibits lysosome-phagosome fusion in human monocytes. J Exp Med, 1983. 158: 2108-2126.
5. Kagan, J. C. and C. R. Roy, *Legionella* phagosomes intercept vesicular traffic from endoplasmic reticulum exit sites. Nat Cell Biol, 2002. 4: 945-54.
6. Derre, I. and R. R. Isberg, *Legionella pneumophila* replication vacuole formation involves rapid recruitment of proteins of the early secretory system. Infect Immun, 2004.72: 3048-53.
7. Kagan, J. C., et al., *Legionella* subvert the functions of rab1 and sec22b to create a replicative organelle. J Exp Med, 2004. 199: 1201-11.
8. Li, Z., J. M. Solomon, and R. R. Isberg, *Dictyostelium discoideum* strains lacking the RtoA protein are defective for maturation of the *Legionella pneumophila* replication vacuole. Cell Microbiol, 2005. 7: 431-42.
9. Lu, H. and M. Clarke, Dynamic properties of *Legionella*-containing phagosomes in *Dictyostelium* amoebae. Cell Microbiol, 2005. 7: 995-1007.
10. Sturgill-Koszycki, S. and M. S. Swanson, *Legionella pneumophila* replication vacuoles mature into acidic, endocytic organelles. J Exp Med, 2000. 192: 1261-1272.
11. Coers, J., C. Monahan, and C. R. Roy, Modulation of phagosome biogenesis by *Legionella pneumophila* creates an organelle permissive for intracellular growth. Nat Cell Biol, 1999. 1: 451-453.
12. Segal, G., M. Purcell, and H. A. Shuman, Host cell killing and bacterial conjugation require overlapping sets of genes within a 22-kb region of the *Legionella pneumophila* genome. Proc Natl Acad Sci USA, 1998. 95: 1669-1674.
13. Vogel, J. P., et al., Conjugative transfer by the virulence system of *Legionella pneumophila*. Science, 1998.279: 873-876.
14. Hilbi, H., G. Segal, and H. A. Shuman, Icm/Dot-dependent upregulation of phagocytosis by *Legionella pneumophila*. Mol Microbiol, 2001. 42: 603-17.
15. Watarai, M., et al., *Legionella pneumophila* is internalized by a macropinocytotic uptake pathway controlled by the Dot/Icm system and the mouse ign1 locus. J Exp Med, 2001. 194: 1081-1096.
16. Nagai, H., et al., A bacterial guanine nucleotide exchange factor activates ARF on *Legionella* phagosomes. Science, 2002. 295: 679-82.
17. Conover, G. M., et al., The *Legionella pneumophila* LidA protein: a translocated substrate of the Dot/Icm system associated with maintenance of bacterial integrity. Mol Microbiol, 2003. 48: 305-21.
18. Luo, Z. Q. and R. R. Isberg, Multiple substrates of the *Legionella pneumophila* Dot/Icm system identified by interbacterial protein transfer. Proc Natl Acad Sci USA, 2004. 101: 841-6.
19. Chen, J., et al., *Legionella* effectors that promote nonlytic release from protozoa. Science, 2004.303: 1358-61.
20. Ninio, S., et al., The *Legionella* IcmS-IcmW protein complex is important for Dot/Icm-mediated protein translocation. Mol Microbiol, 2005. 55: 912-26.
21. Shohdy, N., et al., Pathogen effector protein screening in yeast identifies *Legionella* factors that interfere with membrane trafficking. Proc Natl Acad Sci USA, 2005. 102: 4866-71.
22. Campodonico, E. M., L. Chesnel, and C. R. Roy, A yeast genetic system for the identification and characterization of substrate proteins transferred into host cells by the *Legionella pneumophila* Dot/Icm system. Mol Microbiol, 2005. 56: 918-33.
23. Gillooly, D. J., A. Simonsen, and H. Stenmark, Phosphoinositides and phagocytosis. J Cell Biol, 2001. 155: 15-18.
24. De Matteis, M. A. and A. Godi, PI-loting membrane traffic. Nat Cell Biol, 2004. 6: 487-92.
25. Pizarro-Cerda, J. and P. Cossart, Subversion of phosphoinositide metabolism by intracellular bacterial pathogens. Nat Cell Biol, 2004. 6: 1026-33.
26. Niebuhr, K., et al., Conversion of PtdIns(4,5)P(2) into PtdIns(5)P by the *S. flexneri* effector IpgD reorganizes host cell morphology. EMBO J, 2002. 21: 5069-78.
27. Terebiznik, M. R., et al., Elimination of host cell PtdIns (4,5)P(2) by bacterial SigD promotes membrane fission during invasion by *Salmonella*. Nat Cell Biol, 2002. 4: 766-73.
28. Hernandez, L. D., et al., *Salmonella* modulates vesicular traffic by altering phosphoinositide metabolism. Science, 2004. 304: 1805-7.
29. Van Haastert, P. J. and P. N. Devreotes, Chemotaxis: signalling the way forward. Nat Rev Mol Cell Biol, 2004. 5: 626-34.
30. Chung, C. Y., S. Funamoto, and R. A. Firtel, Signaling pathways controlling cell polarity and chemotaxis. Trends Biochem Sci, 2001. 26: 557-66.
31. Solomon, J. M., et al., Intracellular growth of *Legionella pneumophila* in *Dictyostelium discoideum*, a system for genetic analysis of host-pathogen interactions. Infect Immun, 2000. 68: 2939-2947.
32. Hagele, S., et al., *Dictyostelium discoideum*: a new host model system for intracellular pathogens of the genus *Legionella*. Cell Microbiol, 2000. 2: 165-71.
33. Otto, G. P., et al., Macroautophagy is dispensable for intracellular replication of *Legionella pneumophila* in *Dictyostelium discoideum*. Mol Microbiol, 2004. 51: 63-72.
34. Zhou, K., et al., A phosphatidylinositol (PI) kinase gene family in *Dictyostelium discoideum*: biological roles of putative mammalian p110 and yeast Vps34p PI3-kinase homologs during growth and development. Mol Cell Biol, 1995. 15: 5645-5656.
35. Khelef, N., H. A. Shuman, and F. R. Maxfield, Phagocytosis of wild-type *Legionella pneumophila* occurs through a wortmannin-insensitive pathway. Infect Immun, 2001. 69: 5157-5161.
36. Zhou, K., et al., Disruption of *Dictyostelium* PI3K genes reduces [$^{32}$P]phosphatidylinositol 3,4 bisphosphate and [$^{32}$P]phosphatidylinositol trisphosphate levels, alters F-actin distribution and impairs pinocytosis. J Cell Sci, 1998. 111: 283-294.
37. Eichinger, L., et al., The genome of the social amoeba *Dictyostelium discoideum*. Nature, 2005. 435: 43-57.
38. Rupper, A. C., et al., p110-related PI 3-kinases regulate phagosome-phagosome fusion and phagosomal pH through a PKB/Akt dependent pathway in *Dictyostelium*. J Cell Sci, 2001. 114: 1283-95.
39. Chien, M., et al., The genomic sequence of the accidental pathogen *Legionella pneumophila*. Science, 2004. 305: 1966-8.
40. Cazalet, C., et al., Evidence in the *Legionella pneumophila* genome for exploitation of host cell functions and high genome plasticity. Nat Genet, 2004. 36: 1165-73.
41. Feeley, J. C., et al., Charcoal-yeast extract agar: primary isolation medium for *Legionella pneumophila*. J Clin Microbiol, 1979. 10: 437-441.
42. Horwitz, M. A. and S. C. Silverstein, Intracellular multiplication of Legionnaires' disease bacteria (*Legionella pneumophila*) in human monocytes is reversibly inhibited by erythromycin and rifampin. J Clin Invest, 1983. 71: 15-26.

43. Buczynski, G., et al., Inactivation of two *Dictyostelium discoideum* genes, DdPIK1 and DdPIK2, encoding proteins related to mammalian phosphatidylinositide 3-kinases, results in defects in endocytosis, lysosome to postlysosome transport, and actin cytoskeleton organization. J Cell Biol, 1997. 136: 1271-1286.
44. Sussman, M., Cultivation and synchronous morphogenesis of *Dictyostelium* under controlled experimental conditions. Methods Cell Biol, 1987. 28: 9-29.
45. Harlow, E. and D. Lane. Using antibodies. A laboratory manual. 1999, Plainview, N.Y.: Cold Spring Harbor Laboratory Press. 311-314.
46. Albers, U., et al., The amoebae plate test implicates a paralogue of lpxB in the interaction of *Legionella pneumophila* with *Acanthamoeba castellanii*. Microbiology, 2005. 151: 167-82.
47. Woscholski, R., et al., A comparison of demethoxyviridin and wortmannin as inhibitors of phosphatidylinositol 3-kinase. FEBS Lett, 1994. 342: 109-14.
48. Obert, S., et al., The adenovirus E4-6/7 protein transactivates the E2 promoter by inducing dimerization of a heteromeric E2F complex. Mol Cell Biol, 1994. 14: 1333-46.
49. Dowler, S., et al., Identification of pleckstrin-homology-domain-containing proteins with novel phosphoinositide-binding specificities. Biochem J, 2000. 351: 19-31.
50. Sadosky, A. B., L. A. Wiater, and H. A. Shuman, Identification of *Legionella pneumophila* genes required for growth within and killing of human macrophages. Infect Immun, 1993. 61: 5361-5373.
51. Segal, G. and H. A. Shuman, Intracellular multiplication and human macrophage killing by *Legionella pneumophila* are inhibited by conjugal components of IncQ plasmid RSF1010. Mol Microbiol, 1998.30: 197-208.
52. Muller-Taubenberger, A., et al., Calreticulin and calnexin in the endoplasmic reticulum are important for phagocytosis. EMBO J, 2001. 20: 6772-6782.
53. Mampel, J., et al., Planktonic replication is essential for biofilm formation of *Legionella pneumophila* in a complex medium under static and dynamic flow conditions. Appl Environ Microbiol, 72: 2885-2895.
54. Godi A, Di Campli A, Konstantakopoulos A, Di Tullio G, Alessi D R, et al. (2004) FAPPs control Golgi-to-cell-surface membrane traffic by binding to ARF and PtdIns(4)P. Nat Cell Biol 6: 393-404.
55. Lowe, M. (2005) Structure and function of the Lowe syndrome protein OCRL1. Traffic 6: 711-719.

I claim:

1. A method for determining the presence or absence of a phosphoinositide lipid in a sample, the method comprising:
   i) contacting the sample with a polypeptide comprising a sequence selected from the group consisting of:
      a) SEQ ID NO: 1 and
      b) *Legionella pneumophila* SidC encoded by SEQ ID NO: 3; and
   ii) determining whether the compound binds to the phosphoinositide lipid, wherein the phosphoinositide lipid is phosphatidylinositol (4) phosphate.

2. The method of claim 1, wherein the polypeptide is fused with or conjugated to a tag.

3. The method of claim 2, wherein the tag is selected from the group consisting of: GST, M45, Myc, HA, His, fluorescent proteins, fluorophores, biotin, avidin-peroxidase, avidin-fluorophor and colloidal gold.

4. The method of claim 1, wherein binding of the polypeptide to the phosphoinositide lipid is detected by antibody, fluorescence or electron microscopy.

5. A method for quantifying the amount of a phosphoinositide lipid in a sample, the method comprising:
  i) contacting the sample with a polypeptide comprising a sequence selected from the group consisting of:
    a) SEQ ID NO: 1 and
    b) *Legionella pneumophila* SidC encoded by SEQ ID NO: 3; and
  ii) determining whether the compounds binds to the phosphoinositide lipid; and
  iii) quantifying the amount of bound phosphoinositide lipid,
  wherein the phosphoinositide lipid is phosphatidylinositol 94) phosphate.

6. The method of claim 5, wherein the polypeptide is fused with or conjugated to a tag.

7. The method of claim 6, wherein the tag is selected from the group consisting of: GST, M45, Myc, HA, His, fluorescent proteins, fluorophores, biotin, avidin-peroxidase, avidin-fluorophor and colloidal gold.

8. The method of claim 5, wherein binding of the polypeptide to the phosphoinositide lipid is detected by antibody, fluorescence or electron microscopy.

* * * * *

UNITED STATES PATENT AND TRADEMARK OFFICE
CERTIFICATE OF CORRECTION

PATENT NO. : 7,629,130 B2  Page 1 of 1
APPLICATION NO. : 11/525334
DATED : December 8, 2009
INVENTOR(S) : Hubert Hilbi It is certified that error appears in the above-identified patent and that said Letters Patent is hereby corrected as shown below:

| Col. No. | Line(s) | Edits |
|---|---|---|
| 60 | 4 | Replace "94) phosphate." with --(4) phosphate-- |

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,629,130 B2 |
| APPLICATION NO. | : 11/525334 |
| DATED | : December 8, 2009 |
| INVENTOR(S) | : Hubert Hilbi |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 347 days.

Signed and Sealed this

Second Day of November, 2010

David J. Kappos
*Director of the United States Patent and Trademark Office*